US011793515B2

(12) United States Patent
Shelton, V et al.

(10) Patent No.: US 11,793,515 B2
(45) Date of Patent: Oct. 24, 2023

(54) SURGICAL STAPLER BUTTRESS ASSEMBLY WITH ADHESION TO WET END EFFECTOR

(71) Applicant: Cilag GmbH International, Zug (CH)

(72) Inventors: Frederick E. Shelton, V, Hillsboro, OH (US); Michael J. Vendely, Lebanon, OH (US); Prudence A. Turner, Warsaw, IN (US); Jackie J. Donners, Pennington, NJ (US); Mark D. Timmer, Jersey City, NJ (US); Rao Bezwada, Whitehouse Station, NJ (US); Aidan Craigwood, Cambridge (GB); Caroline Hagerman, Cambridge (GB); Ashley Easter, Cambridge (GB); Kathrin Holtzmann, Cambridge (GB)

(73) Assignee: Cilag GmbH International, Zug (CH)

( * ) Notice: Subject to any disclaimer, the term of this patent is extended or adjusted under 35 U.S.C. 154(b) by 263 days.

(21) Appl. No.: 17/084,994

(22) Filed: Oct. 30, 2020

(65) Prior Publication Data
US 2021/0113205 A1 Apr. 22, 2021

Related U.S. Application Data

(63) Continuation of application No. 16/727,348, filed on Dec. 26, 2019, now Pat. No. 11,234,699, which is a
(Continued)

(51) Int. Cl.
*A61B 17/072* (2006.01)
*B29C 65/48* (2006.01)
(Continued)

(52) U.S. Cl.
CPC ...... *A61B 17/072* (2013.01); *A61B 17/07207* (2013.01); *A61B 17/07292* (2013.01);
(Continued)

(58) Field of Classification Search
CPC ............ A61B 17/072; A61B 17/07207; A61B 17/07292; A61B 2017/00004;
(Continued)

(56) References Cited

U.S. PATENT DOCUMENTS

| 4,805,823 A | 2/1989 | Rothfuss |
| 5,415,334 A | 5/1995 | Williamson, et al. |

(Continued)

FOREIGN PATENT DOCUMENTS

| EP | 1520525 A1 | 4/2005 |
| EP | 2759269 A1 | 7/2014 |

(Continued)

OTHER PUBLICATIONS

Chinese Office Action and Search Report dated Jun. 12, 2020 for Application No. 201680063836.3, 15 pages.
(Continued)

*Primary Examiner* — Philip C Tucker
*Assistant Examiner* — Brian R Slawski
(74) *Attorney, Agent, or Firm* — Frost Brown Todd LLP

(57) ABSTRACT

A buttress assembly is configured to temporarily adhere to a wet surgical stapler end effector. The buttress assembly includes a buttress body and a humidity tolerant adhesive material. The humidity tolerant adhesive material is applied to at least one side of the buttress body. The humidity tolerant adhesive material is configured to hold the buttress body to an underside of an anvil or a deck of a staple cartridge for at least five minutes in an environment of 100% relative humidity at approximately 37° C.

20 Claims, 9 Drawing Sheets

Related U.S. Application Data continuation of application No. 14/926,057, filed on Oct. 29, 2015, now Pat. No. 10,517,592.

(51) Int. Cl.
| | | |
|---|---|---|
| *B29C 65/00* | (2006.01) | |
| *B29C 65/52* | (2006.01) | |
| *A61B 17/00* | (2006.01) | |
| *B29L 31/00* | (2006.01) | |

(52) U.S. Cl.
CPC .... *B29C 65/48* (2013.01); *A61B 2017/00004* (2013.01); *A61B 2017/00938* (2013.01); *A61B 2017/00951* (2013.01); *A61B 2017/07257* (2013.01); *A61B 2017/07285* (2013.01); *B29C 65/4825* (2013.01); *B29C 65/52* (2013.01); *B29C 66/8324* (2013.01); *B29C 66/8614* (2013.01); *B29L 2031/7546* (2013.01)

(58) Field of Classification Search
CPC ........... A61B 2017/00938; A61B 2017/00951; A61B 2017/07257; A61B 2017/07285; B29C 65/48; B29C 65/4825; B29C 65/52; B29C 66/8324; B29C 66/8614; B29L 2031/7546
USPC ....... 156/60, 91, 92, 94, 250, 252, 325, 326, 156/327, 332, 328; 227/175.1, 176.1, 227/178.1, 179.1, 180.1, 19; 606/219, 606/220
See application file for complete search history.

(56) References Cited

U.S. PATENT DOCUMENTS

| | | | |
|---|---|---|---|
| 5,465,895 A | 11/1995 | Knodel et al. | |
| 5,597,107 A | 1/1997 | Knodel et al. | |
| 5,632,432 A | 5/1997 | Schulze et al. | |
| 5,673,840 A | 10/1997 | Schulze et al. | |
| 5,704,534 A | 1/1998 | Huitema et al. | |
| 5,752,965 A | 5/1998 | Francis et al. | |
| 5,792,135 A | 8/1998 | Madhani et al. | |
| 5,814,055 A | 9/1998 | Knodel et al. | |
| 5,817,084 A | 10/1998 | Jensen | |
| 5,878,193 A | 3/1999 | Wang et al. | |
| 6,231,565 B1 | 5/2001 | Tovey et al. | |
| 6,325,810 B1* | 12/2001 | Hamilton | A61B 17/07207 606/151 |
| 6,364,888 B1 | 4/2002 | Niemeyer et al. | |
| 6,592,597 B2* | 7/2003 | Grant | A61B 17/072 623/1.42 |
| 6,783,524 B2 | 8/2004 | Anderson et al. | |
| 6,978,921 B2 | 12/2005 | Shelton, IV et al. | |
| 7,000,818 B2 | 2/2006 | Shelton, IV et al. | |
| 7,143,923 B2 | 12/2006 | Shelton, IV et al. | |
| 7,303,108 B2 | 12/2007 | Shelton, IV | |
| 7,367,485 B2 | 5/2008 | Shelton, IV et al. | |
| 7,380,695 B2 | 6/2008 | Doll et al. | |
| 7,380,696 B2 | 6/2008 | Shelton, IV et al. | |
| 7,404,508 B2 | 7/2008 | Smith et al. | |
| 7,434,715 B2 | 10/2008 | Shelton, IV et al. | |
| 7,524,320 B2 | 4/2009 | Tierney et al. | |
| 7,691,098 B2 | 4/2010 | Wallace et al. | |
| 7,721,930 B2 | 5/2010 | McKenna et al. | |
| 7,806,891 B2 | 10/2010 | Nowlin et al. | |
| 8,141,762 B2 | 3/2012 | Bedi et al. | |
| 8,210,411 B2 | 7/2012 | Yates et al. | |
| 8,371,491 B2 | 2/2013 | Huitema et al. | |
| 8,408,439 B2 | 4/2013 | Huang et al. | |
| 8,453,914 B2 | 6/2013 | Laurent et al. | |
| 8,479,969 B2 | 7/2013 | Shelton, IV | |
| 8,573,461 B2 | 11/2013 | Shelton, IV et al. | |
| 8,573,465 B2 | 11/2013 | Shelton, IV | |
| 8,602,288 B2 | 12/2013 | Shelton, IV et al. | |
| 8,616,431 B2 | 12/2013 | Timm et al. | |
| 8,783,541 B2 | 7/2014 | Shelton, IV et al. | |
| 8,800,838 B2 | 8/2014 | Shelton, IV | |
| 8,801,735 B2 | 8/2014 | Shelton, IV et al. | |
| 8,814,025 B2 | 8/2014 | Miller et al. | |
| 8,820,605 B2 | 9/2014 | Shelton, IV | |
| 8,844,789 B2 | 9/2014 | Shelton, IV et al. | |
| 8,899,464 B2 | 12/2014 | Hueil et al. | |
| 8,998,060 B2 | 4/2015 | Bruewer et al. | |
| 9,101,359 B2 | 8/2015 | Smith et al. | |
| 9,186,142 B2 | 11/2015 | Fanelli et al. | |
| 9,198,644 B2 | 12/2015 | Balek et al. | |
| 9,211,120 B2 | 12/2015 | Scheib et al. | |
| 9,301,759 B2 | 4/2016 | Spivey et al. | |
| 9,393,018 B2 | 7/2016 | Wang et al. | |
| 9,398,911 B2 | 7/2016 | Auld | |
| 9,492,170 B2 | 11/2016 | Bear et al. | |
| 9,517,065 B2 | 12/2016 | Simms et al. | |
| 10,433,846 B2 | 10/2019 | Vendely et al. | |
| 10,517,592 B2 | 12/2019 | Shelton, IV et al. | |
| 10,569,071 B2 | 2/2020 | Harris et al. | |
| 10,835,249 B2 | 11/2020 | Schellin et al. | |
| 2002/0165562 A1 | 11/2002 | Grant et al. | |
| 2004/0093029 A1* | 5/2004 | Zubik | A61B 17/072 606/219 |
| 2006/0004407 A1* | 1/2006 | Hiles | A61B 17/0644 606/215 |
| 2008/0169328 A1 | 7/2008 | Shelton, IV | |
| 2009/0120994 A1 | 5/2009 | Murray et al. | |
| 2009/0157087 A1 | 6/2009 | Wei et al. | |
| 2009/0206143 A1* | 8/2009 | Huitema | A61B 17/07292 227/176.1 |
| 2010/0234861 A1 | 9/2010 | Oray et al. | |
| 2012/0241493 A1 | 9/2012 | Baxter, III et al. | |
| 2013/0062391 A1 | 3/2013 | Boudreaux et al. | |
| 2013/0068816 A1 | 3/2013 | Vasudevan et al. | |
| 2013/0075447 A1 | 3/2013 | Weisenburgh, et al. | |
| 2013/0206813 A1 | 8/2013 | Nalagatla | |
| 2013/0261660 A1 | 10/2013 | McKay | |
| 2014/0209658 A1* | 7/2014 | Skalla | A61B 17/1155 227/175.1 |
| 2014/0239036 A1 | 8/2014 | Zerkle et al. | |
| 2014/0239037 A1 | 8/2014 | Boudreaux et al. | |
| 2014/0239038 A1 | 8/2014 | Leimbach et al. | |
| 2014/0239040 A1 | 8/2014 | Fanelli et al. | |
| 2014/0239041 A1 | 8/2014 | Zerkle et al. | |
| 2014/0239043 A1 | 8/2014 | Simms et al. | |
| 2014/0239044 A1 | 8/2014 | Hoffman | |
| 2014/0263563 A1 | 9/2014 | Stokes et al. | |
| 2015/0272575 A1 | 10/2015 | Leimbach et al. | |
| 2015/0351754 A1 | 12/2015 | Harris et al. | |
| 2015/0351758 A1 | 12/2015 | Shelton, IV et al. | |
| 2015/0351763 A1 | 12/2015 | Shelton, IV et al. | |
| 2015/0374360 A1 | 12/2015 | Scheib et al. | |
| 2015/0374373 A1 | 12/2015 | Rector et al. | |
| 2016/0089146 A1 | 3/2016 | Harris et al. | |
| 2016/0278774 A1 | 9/2016 | Shelton, IV et al. | |
| 2017/0086842 A1 | 3/2017 | Shelton, IV et al. | |
| 2020/0187940 A1 | 6/2020 | Shelton, IV et al. | |

FOREIGN PATENT DOCUMENTS

| | | |
|---|---|---|
| EP | 3072460 A2 | 9/2016 |
| JP | 2008-505685 A | 2/2008 |
| JP | 2015-523139 A | 8/2015 |

OTHER PUBLICATIONS

European Search Report and Written Opinion dated Feb. 16, 2017 for Application No. 16196246.9, 9 pages.
European Examination Report dated Jan. 17, 2019 for Application No. 16196246.9, 5 pages.
European Communication dated Dec. 14, 2020 for Application No. 16196246.9, 6 pages.
International Search Report and Written Opinion dated Feb. 16, 2017 for International Application No. PCT/US2016/058401, 12 pages.

(56) References Cited

OTHER PUBLICATIONS

Japanese Notification of Reasons for Refusal dated Sep. 18, 2020 for Application No. 2018-522085, 5 pages.
U.S. Appl. No. 62/209,041, filed Aug. 24, 2015.

* cited by examiner

SURGICAL STAPLER BUTTRESS ASSEMBLY WITH ADHESION TO WET END EFFECTOR

This application is a continuation of U.S. patent application Ser. No. 16/727,348, entitled "Surgical Stapler Buttress Assembly with Adhesion to Wet End Effector," filed on Dec. 26, 2019 and published as U.S. Patent Publication No. 2020.0187940 on Jun. 18, 2020, issued as U.S. Pat. No. 11,234,699 on Feb. 1, 2022, which is a continuation of U.S. patent application Ser. No. 14/926,057, entitled "Surgical Stapler Buttress Assembly with Adhesion to Wet End Effector," filed on Oct. 29, 2015 and issued as U.S. Pat. No. 10,517,592 on Dec. 31, 2019.

BACKGROUND

In some settings, endoscopic surgical instruments may be preferred over traditional open surgical devices since a smaller incision may reduce the post-operative recovery time and complications. Consequently, some endoscopic surgical instruments may be suitable for placement of a distal end effector at a desired surgical site through the cannula of a trocar. These distal end effectors may engage tissue in a number of ways to achieve a diagnostic or therapeutic effect (e.g., endocutter, grasper, cutter, stapler, clip applier, access device, drug/gene therapy delivery device, and energy delivery device using ultrasonic vibration, RF, laser, etc.). Endoscopic surgical instruments may include a shaft between the end effector and a handle portion, which is manipulated by the clinician. Such a shaft may enable insertion to a desired depth and rotation about the longitudinal axis of the shaft, thereby facilitating positioning of the end effector within the patient. Positioning of an end effector may be further facilitated through inclusion of one or more articulation joints or features, enabling the end effector to be selectively articulated or otherwise deflected relative to the longitudinal axis of the shaft.

Examples of endoscopic surgical instruments include surgical staplers. Some such staplers are operable to clamp down on layers of tissue, cut through the clamped layers of tissue, and drive staples through the layers of tissue to substantially seal the severed layers of tissue together near the severed ends of the tissue layers. Merely exemplary surgical staplers are disclosed in U.S. Pat. No. 4,805,823, entitled "Pocket Configuration for Internal Organ Staplers," issued Feb. 21, 1989; U.S. Pat. No. 5,415,334, entitled "Surgical Stapler and Staple Cartridge," issued May 16, 1995; U.S. Pat. No. 5,465,895, entitled "Surgical Stapler Instrument," issued Nov. 14, 1995; U.S. Pat. No. 5,597,107, entitled "Surgical Stapler Instrument," issued Jan. 28, 1997; U.S. Pat. No. 5,632,432, entitled "Surgical Instrument," issued May 27, 1997; U.S. Pat. No. 5,673,840, entitled "Surgical Instrument," issued Oct. 7, 1997; U.S. Pat. No. 5,704,534, entitled "Articulation Assembly for Surgical Instruments," issued Jan. 6, 1998; U.S. Pat. No. 5,814,055, entitled "Surgical Clamping Mechanism," issued Sep. 29, 1998; U.S. Pat. No. 6,978,921, entitled "Surgical Stapling Instrument Incorporating an E-Beam Firing Mechanism," issued Dec. 27, 2005; U.S. Pat. No. 7,000,818, entitled "Surgical Stapling Instrument Having Separate Distinct Closing and Firing Systems," issued Feb. 21, 2006; U.S. Pat. No. 7,143,923, entitled "Surgical Stapling Instrument Having a Firing Lockout for an Unclosed Anvil," issued Dec. 5, 2006; U.S. Pat. No. 7,303,108, entitled "Surgical Stapling Instrument Incorporating a Multi-Stroke Firing Mechanism with a Flexible Rack," issued Dec. 4, 2007; U.S. Pat. No. 7,367,485, entitled "Surgical Stapling Instrument Incorporating a Multistroke Firing Mechanism Having a Rotary Transmission," issued May 6, 2008; U.S. Pat. No. 7,380,695, entitled "Surgical Stapling Instrument Having a Single Lockout Mechanism for Prevention of Firing," issued Jun. 3, 2008; U.S. Pat. No. 7,380,696, entitled "Articulating Surgical Stapling Instrument Incorporating a Two-Piece E-Beam Firing Mechanism," issued Jun. 3, 2008; U.S. Pat. No. 7,404,508, entitled "Surgical Stapling and Cutting Device," issued Jul. 29, 2008; U.S. Pat. No. 7,434,715, entitled "Surgical Stapling Instrument Having Multistroke Firing with Opening Lockout," issued Oct. 14, 2008; U.S. Pat. No. 7,721,930, entitled "Disposable Cartridge with Adhesive for Use with a Stapling Device," issued May 25, 2010; U.S. Pat. No. 8,408,439, entitled "Surgical Stapling Instrument with An Articulatable End Effector," issued Apr. 2, 2013; and U.S. Pat. No. 8,453,914, entitled "Motor-Driven Surgical Cutting Instrument with Electric Actuator Directional Control Assembly," issued Jun. 4, 2013. The disclosure of each of the above-cited U.S. Patents is incorporated by reference herein.

While the surgical staplers referred to above are described as being used in endoscopic procedures, it should be understood that such surgical staplers may also be used in open procedures and/or other non-endoscopic procedures. By way of example only, a surgical stapler may be inserted through a thoracotomy, and thereby between a patient's ribs, to reach one or more organs in a thoracic surgical procedure that does not use a trocar as a conduit for the stapler. Such procedures may include the use of the stapler to sever and close a vessel leading to a lung. For instance, the vessels leading to an organ may be severed and closed by a stapler before removal of the organ from the thoracic cavity. Of course, surgical staplers may be used in various other settings and procedures.

Examples of surgical staplers that may be particularly suited for use through a thoracotomy are disclosed in U.S. Patent Pub. No. 2014/0243801, entitled "Surgical Instrument End Effector Articulation Drive with Pinion and Opposing Racks," published Aug. 28, 2014; issued as U.S. Pat. No. 9,186,142 on Nov. 17, 2015; U.S. Patent Pub. No. 2014/0239041, entitled "Lockout Feature for Movable Cutting Member of Surgical Instrument," published Aug. 28, 2014; issued as U.S. Pat. No. 9,717,497 on Aug. 1, 2017; U.S. Patent Pub. No. 2014/0239042, entitled "Integrated Tissue Positioning and Jaw Alignment Features for Surgical Stapler," published Aug. 28, 2014; issued as U.S. Pat. No. 9,517,065 on Dec. 13, 2016; U.S. Patent Pub. No. 2014/0239036, entitled "Jaw Closure Feature for End Effector of Surgical Instrument," published Aug. 28, 2014, issued as U.S. Pat No 9,839,421 on Dec. 12, 2017; U.S. Patent Pub. No. 2014/0239040, entitled "Surgical Instrument with Articulation Lock having a Detenting Binary Spring," published Aug. 28, 2014, issued as U.S. Pat. No. 9,867,615 on Jan. 16, 2018; U.S. Patent Pub. No. 2014/0239043, entitled "Distal Tip Features for End Effector of Surgical Instrument," published Aug. 28, 2014, issued as U.S. Pat. No. 9,622,746 on Apr. 18, 2017; U.S. Patent Pub. No. 2014/0239037, entitled "Staple Forming Features for Surgical Stapling Instrument," published Aug. 28, 2014, issued as U.S. Pat. No. 10,092,292 on Oct. 9, 2018; U.S. Patent Pub. No. 2014/0239038, entitled "Surgical Instrument with Multi-Diameter Shaft," published Aug. 28, 2014, issued as U.S. Pat. No. 9,795,379 on Oct. 24, 2017; and U.S. Patent Pub. No. 2014/0239044, entitled "Installation Features for Surgical Instrument End Effector Cartridge," published Aug. 28, 2014, issued as U.S. Pat. No. 9,808,248 on Nov. 7, 2017.

The disclosure of each of the above-cited U.S. Patent Publications is incorporated by reference herein.

Additional surgical stapling instruments are disclosed in U.S. Pat. No. 8,801,735, entitled "Surgical Circular Stapler with Tissue Retention Arrangements," issued Aug. 12, 2014; U.S. Pat. No. 8,141,762, entitled "Surgical Stapler Comprising a Staple Pocket," issued Mar. 27, 2012; U.S. Pat. No. 8,371,491, entitled "Surgical End Effector Having Buttress Retention Features," issued Feb. 12, 2013; U.S. Pub. No. 2014/0263563, entitled "Method and Apparatus for Sealing End-to-End Anastomosis" published Sep. 18, 2014, issued as U.S. Pat. No. 0,597,082 on Mar. 21, 2017; U.S. Pub. No. 2014/0246473, entitled "Rotary Powered Surgical Instruments with Multiple Degrees of Freedom," published Sep. 4, 2014, issued on U.S. Pat. No. 9,398,911 on Jul. 26, 2016; U.S. Pub. No. 2013/0206813, entitled "Linear Stapler," published Aug. 15, 2013, now abondoned; U.S. Pub. No. 2008/0169328, entitled "Buttress Material for Use with a Surgical Stapler," published Jul. 17, 2008, now abandoned; U.S. patent application Ser. No. 14/300,804, entitled "Woven and Fibrous Materials for Reinforcing a Staple Line," filed Jun. 10, 2014, issued as U.S. Pat. No. 9,848,871 on Dec. 26, 2017; U.S. patent application Ser. No. 14/300,811, entitled "Devices and Methods for Sealing Staples in Tissue", issued on U.S. Pat. No. 9,936,954 on Apr. 10, 2018; and U.S. patent application Ser. No. 14/498,070, entitled "Radically Expandable Staple Line" filed Sep. 26, 2014, issued as U.S. Pat. No. 10,426,476 on Oct. 1, 2019. The disclosure of each of the above-cited U.S. Patents, U.S. Patent Publications, and U.S. Patent Applications is incorporated by reference herein.

In some instances, it may be desirable to equip a surgical stapling instrument with a buttress material to reinforce the mechanical fastening of tissue provided by staples. Such a buttress may prevent the applied staples from pulling through tissue and may otherwise reduce a risk of tissue tearing at or near the site of applied staples.

While various kinds of surgical stapling instruments and associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

Figure 1:
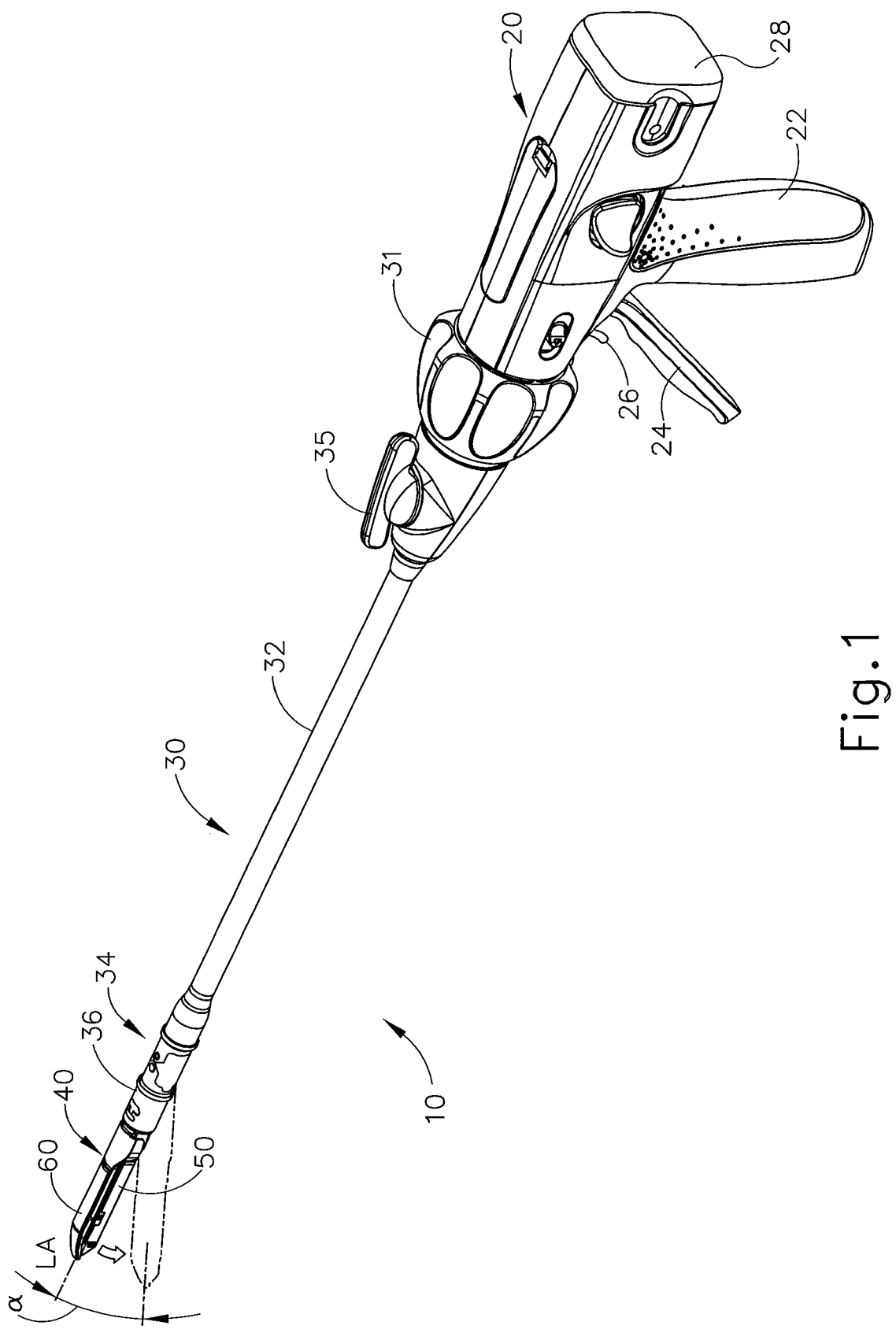
FIG. 1 depicts a perspective view of an exemplary articulating surgical stapling instrument.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

I. EXEMPLARY SURGICAL STAPLER

FIG. 1 depicts an exemplary surgical stapling and severing instrument (10) that includes a handle assembly (20), a shaft assembly (30), and an end effector (40). End effector (40) and the distal portion of shaft assembly (30) are sized for insertion, in a nonarticulated state as depicted in FIG. 1, through a trocar cannula to a surgical site in a patient for performing a surgical procedure. By way of example only, such a trocar may be inserted in a patient's abdomen, between two of the patient's ribs, or elsewhere. In some settings, instrument (10) is used without a trocar. For instance, end effector (40) and the distal portion of shaft assembly (30) may be inserted directly through a thoracotomy or other type of incision. It should be understood that terms such as "proximal" and "distal" are used herein with reference to a clinician gripping handle assembly (20) of instrument (10). Thus, end effector (40) is distal with respect to the more proximal handle assembly (20). It will be further appreciated that for convenience and clarity, spatial terms such as "vertical" and "horizontal" are used herein with respect to the drawings. However, surgical instruments are used in many orientations and positions, and these terms are not intended to be limiting and absolute.

A. Exemplary Handle Assembly and Shaft Assembly

As shown in FIG. 1, handle assembly (20) of the present example comprises pistol grip (22), a closure trigger (24), and a firing trigger (26). Each trigger (24, 26) is selectively pivotable toward and away from pistol grip (22) as will be described in greater detail below. Handle assembly (20) further includes a removable battery pack (28). These components will also be described in greater detail below. Of course, handle assembly (20) may have a variety of other components, features, and operabilities, in addition to or in lieu of any of those noted above. Other suitable configurations for handle assembly (20) will be apparent to those of ordinary skill in the art in view of the teachings herein.

Figure 2:
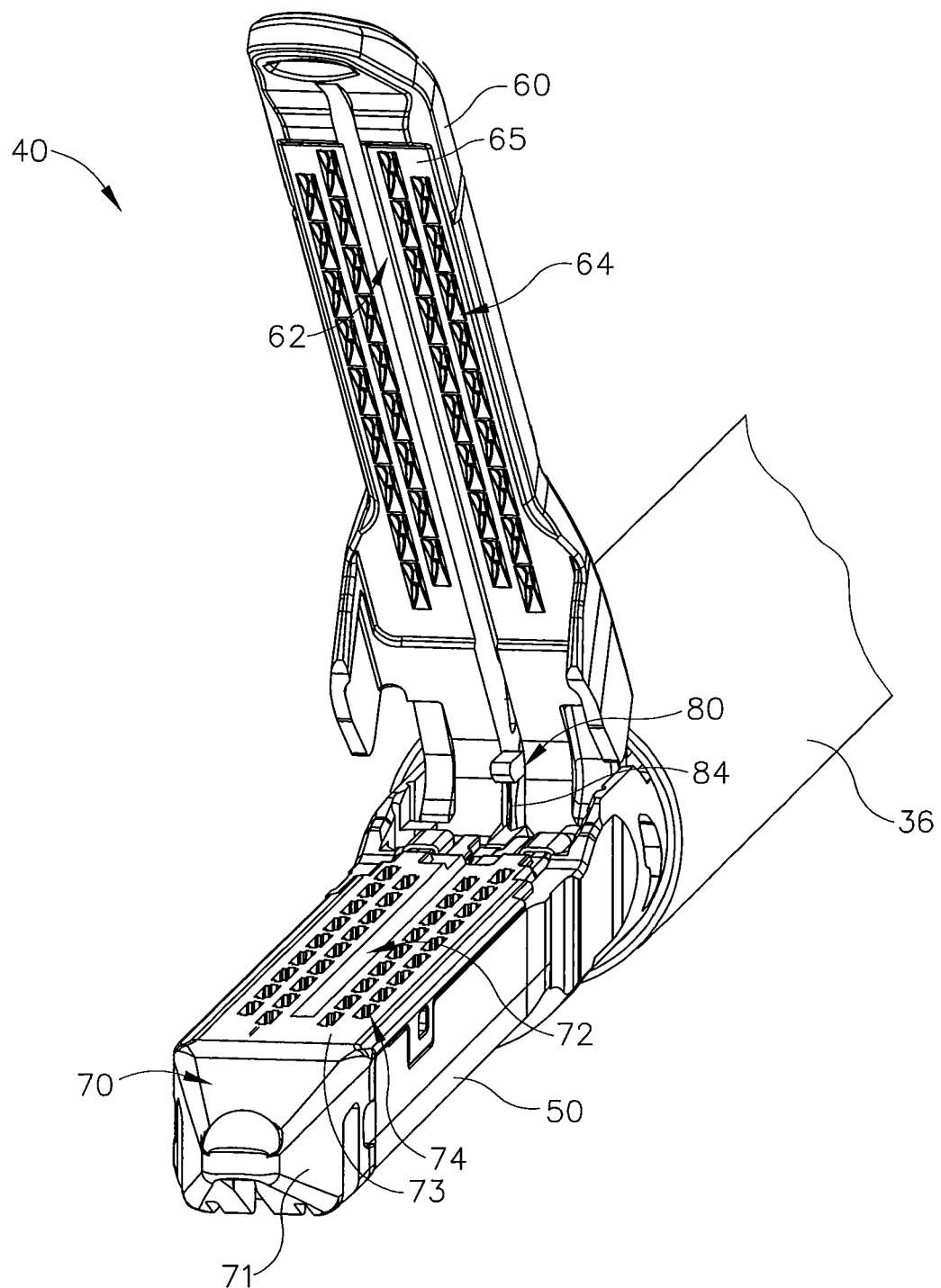
FIG. 2 depicts a perspective view of an end effector of the instrument of FIG. 1, with the end effector in an open configuration.

As shown in FIGS. 1-2, shaft assembly (30) of the present example comprises an outer closure tube (32), an articulation section (34), and a closure ring (36), which is further coupled with end effector (40). Closure tube (32) extends along the length of shaft assembly (30). Closure ring (36) is positioned distal to articulation section (34). Closure tube (32) and closure ring (36) are configured to translate longitudinally relative to handle assembly (20). Longitudinal translation of closure tube (32) is communicated to closure ring (36) via articulation section (34). Exemplary features that may be used to provide longitudinal translation of closure tube (32) and closure ring (36) will be described in greater detail below.

Articulation section (34) is operable to laterally deflect closure ring (36) and end effector (40) laterally away from the longitudinal axis (LA) of shaft assembly (30) at a desired angle (a). In the present example, articulation is controlled through an articulation control knob (35) which is located at the proximal end of shaft assembly (30). Closure ring (36) and end effector (40) pivot about an axis that is perpendicular to the longitudinal axis (LA) of shaft assembly (30) in response to rotation of knob (35). Articulation section (34) is configured to communicate longitudinal translation of closure tube (32) to closure ring (36), regardless of whether articulation section (34) is in a straight configuration or an articulated configuration. By way of example only, articulation section (34) and/or articulation control knob (35) may be constructed and operable in accordance with at least some of the teachings of U.S. Pub. No. 2014/0243801, entitled "Surgical Instrument End Effector Articulation Drive with Pinion and Opposing Racks," published Aug. 28, 2014, issued as U.S. Pat. No. 9,186,142, on Nov. 17, 2015, the disclosure of which is incorporated by reference herein; and/or U.S. patent application Ser. No. 14/314,125, entitled "Articulation Drive Features for Surgical Stapler," filed Jun. 25, 2014, issued as U.S. Pat. No. 10,292,701 on May 21, 2019, the disclosure of which is incorporated by reference herein; and/or in accordance with the various teachings below. Other suitable forms that articulation section (34) and articulation knob (35) may take will be apparent to those of ordinary skill in the art in view of the teachings herein.

As shown in FIG. 1, shaft assembly (30) of the present example further includes a rotation knob (31). Rotation knob (31) is operable to rotate the entire shaft assembly (30) and end effector (40) relative to handle assembly (20) about the longitudinal axis (LA) of shaft assembly (30). Of course, shaft assembly (30) may have a variety of other components, features, and operabilities, in addition to or in lieu of any of those noted above. By way of example only, at least part of shaft assembly (30) is constructed in accordance with at least some of the teachings of U.S. Pub. No. 2014/0239038, entitled "Surgical Instrument with Multi-Diameter Shaft," published Aug. 28, 2014, issued as U.S. Pat. No. 9,795,379, on Oct. 24, 2017,the disclosure of which is incorporated by reference herein. Other suitable configurations for shaft assembly (30) will be apparent to those of ordinary skill in the art in view of the teachings herein.

B. Exemplary End Effector

Figure 3:
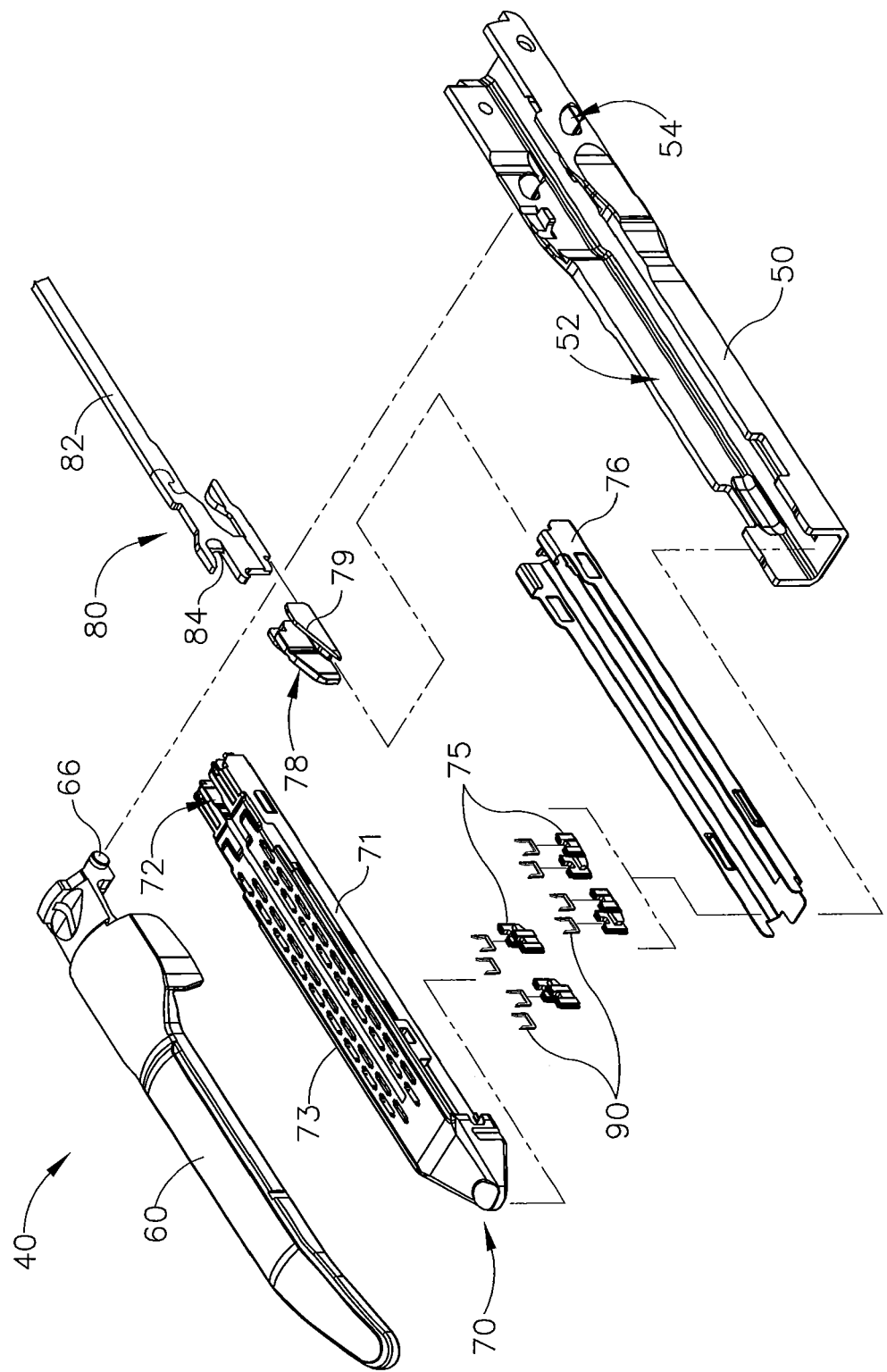
FIG. 3 depicts an exploded perspective view of the end effector of FIG. 2.

As also shown in FIGS. 1-3, end effector (40) of the present example includes a lower jaw (50) and a pivotable anvil (60). Anvil (60) includes a pair of integral, outwardly extending pins (66) that are disposed in corresponding curved slots (54) of lower jaw (50). Anvil (60) is pivotable toward and away from lower jaw (50) between an open position (shown in FIG. 2) and a closed position (shown in FIG. 1). Use of the term "pivotable" (and similar terms with "pivot" as a base) should not be read as necessarily requiring pivotal movement about a fixed axis. For instance, in the present example, anvil (60) pivots about an axis that is defined by pins (66), which slide along curved slots (54) of lower jaw (50) as anvil (60) moves toward lower jaw (50). In such versions, the pivot axis translates along the path defined by slots (54) while anvil (60) simultaneously pivots about that axis. In addition or in the alternative, the pivot axis may slide along slots (54) first, with anvil (60) then pivoting about the pivot axis after the pivot axis has slid a certain distance along the slots (54). It should be understood that such sliding/translating pivotal movement is encompassed within terms such as "pivot," "pivots," "pivotal," "pivotable," "pivoting," and the like. Of course, some versions may provide pivotal movement of anvil (60) about an axis that remains fixed and does not translate within a slot or channel, etc.

As best seen in FIG. 3, lower jaw (50) of the present example defines a channel (52) that is configured to receive a staple cartridge (70). Staple cartridge (70) may be inserted into channel (52), end effector (40) may be actuated, and then staple cartridge (70) may be removed and replaced with another staple cartridge (70). Lower jaw (50) thus releasably retains staple cartridge (70) in alignment with anvil (60) for actuation of end effector (40). In some versions, lower jaw (50) is constructed in accordance with at least some of the teachings of U.S. Pub. No. 2014/0239044, entitled "Installation Features for Surgical Instrument End Effector Cartridge," published Aug. 28, 2014, issued as U.S. Pat. No. 9,808,248, on Nov. 7, 2017, the disclosure of which is incorporated by reference herein. Other suitable forms that lower jaw (50) may take will be apparent to those of ordinary skill in the art in view of the teachings herein.

As best seen in FIGS. 2-3, staple cartridge (70) of the present example comprises a cartridge body (71) and a tray (76) secured to the underside of cartridge body (71). The upper side of cartridge body (71) presents a deck (73), against which tissue may be compressed when anvil (60) is in a closed position. Cartridge body (71) further defines a longitudinally extending channel (72) and a plurality of staple pockets (74). A staple (90) is positioned in each staple pocket (74). A staple driver (75) is also positioned in each staple pocket (74), underneath a corresponding staple (90), and above tray (76). As will be described in greater detail below, staple drivers (75) are operable to translate upwardly in staple pockets (74) to thereby drive staples (90) upwardly through staple pockets (74) and into engagement with anvil (60). Staple drivers (75) are driven upwardly by a wedge sled (78), which is captured between cartridge body (71) and tray (76), and which translates longitudinally through cartridge body (71).

Wedge sled (78) includes a pair of obliquely angled cam surfaces (79), which are configured to engage staple drivers (75) and thereby drive staple drivers (75) upwardly as wedge sled (78) translates longitudinally through cartridge (70). For instance, when wedge sled (78) is in a proximal position, staple drivers (75) are in downward positions and staples

(90) are located in staple pockets (74). As wedge sled (78) is driven to the distal position by a translating knife member (80), wedge sled (78) drives staple drivers (75) upwardly, thereby driving staples (90) out of staple pockets (74) and into staple forming pockets (64) that are formed in the underside (65) of anvil (60). Thus, staple drivers (75) translate along a vertical dimension as wedge sled (78) translates along a horizontal dimension.

In some versions, staple cartridge (70) is constructed and operable in accordance with at least some of the teachings of U.S. Pub. No. 2014/0239042, entitled "Integrated Tissue Positioning and Jaw Alignment Features for Surgical Stapler," published Aug. 28, 2014, issued as U.S. Pat. No. 9,517,065 on Dec. 13, 2016, the disclosure of which is incorporated by reference herein. In addition or in the alternative, staple cartridge (70) may be constructed and operable in accordance with at least some of the teachings of U.S. Pub. No. 2014/0239044, entitled "Installation Features for Surgical Instrument End Effector Cartridge," published Aug. 28, 2014, issued as U.S. Pat. No. 9,808,248, on Nov. 7, 2017, the disclosure of which is incorporated by reference herein. Other suitable forms that staple cartridge (70) may take will be apparent to those of ordinary skill in the art in view of the teachings herein.

As best seen in FIG. 2, anvil (60) of the present example comprises a longitudinally extending channel (62) and a plurality of staple forming pockets (64). Channel (62) is configured to align with channel (72) of staple cartridge (70) when anvil (60) is in a closed position. Each staple forming pocket (64) is positioned to lie over a corresponding staple pocket (74) of staple cartridge (70) when anvil (60) is in a closed position. Staple forming pockets (64) are configured to deform the legs of staples (90) when staples (90) are driven through tissue and into anvil (60). In particular, staple forming pockets (64) are configured to bend the legs of staples (90) to secure the formed staples (90) in the tissue. Anvil (60) may be constructed in accordance with at least some of the teachings of U.S. Pub. No. 2014/0239042, entitled "Integrated Tissue Positioning and Jaw Alignment Features for Surgical Stapler," published Aug. 28, 2014, issued as U.S. Pat. No. 9,517,065 on Dec. 13, 2016; at least some of the teachings of U.S. Pub. No. 2014/0239036, entitled "Jaw Closure Feature for End Effector of Surgical Instrument," published Aug. 28, 2014, issued as U.S. Pat. No. 9,839,421 on Dec. 12, 2017; and/or at least some of the teachings of U.S. Pub. No. 2014/0239037, entitled "Staple Forming Features for Surgical Stapling Instrument," published Aug. 28, 2014, issued as U.S. Pat. No. 10,092,292 on Oct. 9, 2018, the disclosure of which is incorporated by reference herein. Other suitable forms that anvil (60) may take will be apparent to those of ordinary skill in the art in view of the teachings herein.

In the present example, a knife member (80) is configured to translate through end effector (40). As best seen in FIG. 3, knife member (80) is secured to the distal end of a firing beam (82), which extends through a portion of shaft assembly (30). As best seen in FIG. 2, knife member (80) is positioned in channels (62, 72) of anvil (60) and staple cartridge (70). Knife member (80) includes a distally presented cutting edge (84) that is configured to sever tissue that is compressed between anvil (60) and deck (73) of staple cartridge (70) as knife member (80) translates distally through end effector (40). As noted above, knife member (80) also drives wedge sled (78) distally as knife member (80) translates distally through end effector (40), thereby driving staples (90) through tissue and against anvil (60) into formation.

C. Exemplary Actuation of End Effector

In the present example, anvil (60) is driven toward lower jaw (50) by advancing closure ring (36) distally relative to end effector (40). Closure ring (36) cooperates with anvil (60) through a camming action to drive anvil (60) toward lower jaw (50) in response to distal translation of closure ring (36) relative to end effector (40). Similarly, closure ring (36) may cooperate with anvil (60) to open anvil (60) away from lower jaw (50) in response to proximal translation of closure ring (36) relative to end effector (40). By way of example only, closure ring (36) and anvil (60) may interact in accordance with at least some of the teachings of U.S. Pub. No. 2014/0239036, entitled "Jaw Closure Feature for End Effector of Surgical Instrument," published Aug. 28, 2014, issued as U.S. Pat. No. 9,839,421 on Dec. 12, 2017, the disclosure of which is incorporated by reference herein; and/or in accordance with at least some of the teachings of U.S. patent application Ser. No. 14/314,108, entitled "Jaw Opening Feature for Surgical Stapler," filed on Jun. 25, 2014, issued as U.S. Pat. No. 10,335,147 on Jul. 2, 2019, the disclosure of which is incorporated by reference herein.

As noted above, handle assembly (20) includes a pistol grip (22) and a closure trigger (24). As also noted above, anvil (60) is closed toward lower jaw (50) in response to distal advancement of closure ring (36). In the present example, closure trigger (24) is pivotable toward pistol grip (22) to drive closure tube (32) and closure ring (36) distally. Various suitable components that may be used to convert pivotal movement of closure trigger (24) toward pistol grip (22) into distal translation of closure tube (32) and closure ring (36) relative to handle assembly (20) will be apparent to those of ordinary skill in the art in view of the teachings herein.

Also in the present example, instrument (10) provides motorized control of firing beam (82). In particular, instrument (10) includes motorized components that are configured to drive firing beam (82) distally in response to pivoting of firing trigger (26) toward pistol grip (22). In some versions, a motor (not shown) is contained in pistol grip (22) and receives power from battery pack (28). This motor is coupled with a transmission assembly (not shown) that converts rotary motion of a drive shaft of the motor into linear translation of firing beam (82). By way of example only, the features that are operable to provide motorized actuation of firing beam (82) may be configured and operable in accordance with at least some of the teachings of U.S. Pat. No. 8,210,411, entitled "Motor-Driven Surgical Instrument," issued Jul. 3, 2012, the disclosure of which is incorporated by reference herein.; U.S. Pat. No. 8,453,914, entitled "Motor-Driven Surgical Cutting Instrument with Electric Actuator Directional Control Assembly," issued Jun. 4, 2013, the disclosure of which is incorporated by reference herein; and/or U.S. patent application Ser. No. 14/226,142, entitled "Surgical Instrument Comprising a Sensor System," filed Mar. 26, 2014, issued as U.S. Pat. No. 9,913,642 on Mar. 13, 2018, the disclosure of which is incorporated by reference herein.

It should also be understood that any other components or features of instrument (10) may be configured and operable in accordance with any of the various references cited herein. Additional exemplary modifications that may be provided for instrument (10) will be described in greater detail below. Various suitable ways in which the below teachings may be incorporated into instrument (10) will be apparent to those of ordinary skill in the art. Similarly, various suitable ways in which the below teachings may be combined with various teachings of the references cited herein will be apparent to those of ordinary skill in the art. It should therefore be understood that the teachings below may be readily incorporated into the various instruments taught in the various references that are cited herein. It should also be understood that the below teachings are not limited to instrument (10) or devices taught in the references cited herein. The below teachings may be readily applied to various other kinds of instruments, including instruments that would not be classified as surgical staplers. Various other suitable devices and settings in which the below teachings may be applied will be apparent to those of ordinary skill in the art in view of the teachings herein.

II. EXEMPLARY BUTTRESS ASSEMBLY FOR SURGICAL STAPLER

In some instances, it may be desirable to equip end effector (40) with a buttress material to reinforce the mechanical fastening of tissue provided by staples (90). Such a buttress may prevent the applied staples (90) from pulling through the tissue and may otherwise reduce a risk of tissue tearing at or near the site of applied staples (90). In addition to or as an alternative to providing structural support and integrity to a line of staples (90), a buttress may provide various other kinds of effects such as spacing or gap-filling, administration of therapeutic agents, and/or other effects. In some instances, a buttress may be provided on deck (73) of staple cartridge (70). In some other instances, a buttress may be provided on the surface of anvil (60) that faces staple cartridge (70). It should also be understood that a first buttress may be provided on deck (73) of staple cartridge (70) while a second buttress is provided on anvil (60) of the same end effector (40). Various examples of forms that a buttress may take will be described in greater detail below. Various ways in which a buttress may be secured to a staple cartridge (70) or an anvil (60) will also be described in greater detail below.

A. Exemplary Composition of Buttress Assembly for Surgical Stapler

Figure 4:
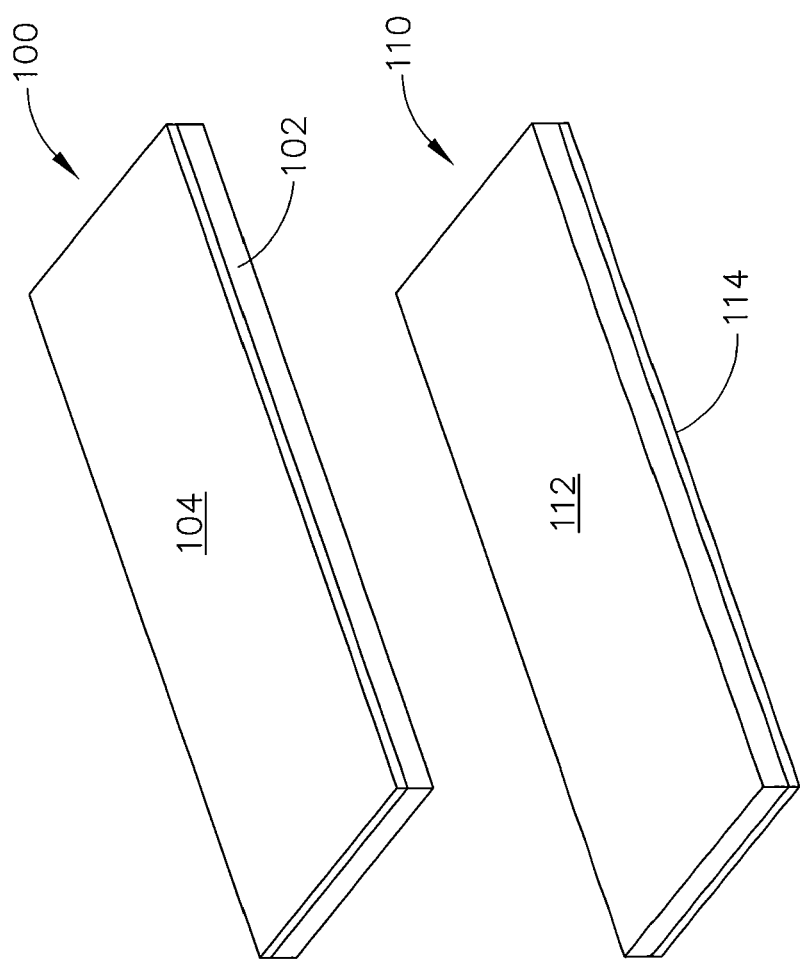
FIG. 4 depicts a perspective view of an exemplary upper buttress and an exemplary lower buttress, each of which may be applied to the end effector of FIG. 2.

FIG. 4 shows an exemplary pair of buttress assemblies (100, 110) with a basic composition. Buttress assembly (100) of this example comprises a buttress body (102) and an upper adhesive layer (104). Similarly, buttress assembly (110) comprises a buttress body (112) and a lower adhesive layer (114). In the present example, each buttress body (102, 112) comprises a strong yet flexible material configured to structurally support a line of staples (90). By way of example only, each buttress body (102, 112) may comprise a mesh of polyglactin 910 material by Ethicon, Inc. of Somerville, N.J. Alternatively, any other suitable materials or combinations of materials may be used in addition to or as an alternative to polyglactin 910 material to form each buttress body (102, 112). Each buttress body (102, 112) may take any other suitable form and may be constructed of any other suitable material(s). By way of further example only, each buttress body (102, 112) may comprise one or more of the following: NEOVEIL absorbable PGA felt by Gunze Limited, of Kyoto, Japan; SEAMGUARD polyglycolic acid:trimethylene carbonate (PGA:TMC) reinforcement material by W.L. Gore & Associates, Inc., of Flagstaff, Ariz.; PERI-STRIPS DRY with VERITAS Collagen Matrix (PSDV) reinforcement material, by Baxter Healthcare Corporation of Deerfield, Ill.; BIODESIGN biologic graft material by Cook Medical, Bloomington, Ind.; and/or SURGICEL NU-KNIT hemostat material by Ethicon, Inc. of Somerville, N.J. Still other suitable materials that may be used to form each buttress body (102, 112) will be apparent to those of ordinary skill in the art in view of the teachings herein.

In addition or in the alternative, each buttress body (102, 112) may comprise a material including, for example, a hemostatic agent such as fibrin to assist in coagulating blood and reduce bleeding at the severed and/or stapled surgical site along tissue (90). As another merely illustrative example, each buttress body (102, 112) may comprise other adjuncts or hemostatic agents such as thrombin may be used such that each buttress body (102, 112) may assist to coagulate blood and reduce the amount of bleeding at the surgical site. Other adjuncts or reagents that may be incorporated into each buttress body (102, 112) may further include but are not limited to medical fluid or matrix components. Merely illustrative examples of materials that may be used to form each buttress body (102, 112), as well as materials that may be otherwise incorporated into each buttress body (102, 112), are disclosed in U.S. patent application Ser. No. 14/667,842, entitled "Method of Applying a Buttress to a Surgical Stapler," filed Mar. 25, 2015, issued as U.S. Pat. No. 10,349,939, on Jul. 16, 2019, the disclosure of which is incorporated by reference herein. Alternatively, any other suitable materials may be used.

By way of further example only, each buttress body (102, 112) may be constructed in accordance with at least some of the teachings of U.S. Patent Pub. No. 2012/0241493, entitled "Tissue Thickness Compensator Comprising Controlled Release and Expansion," published Sep. 27, 2012, issued as U.S. Pat. No. 10,123,798 on Nov. 13, 2018, the disclosure of which is incorporated by reference herein; U.S. Patent Pub. No. 2013/0068816, entitled "Surgical Instrument and Buttress Material," published Mar. 21, 2013, now abandoned, the disclosure of which is incorporated by reference herein; U.S. Patent Pub. No. 2013/0062391, entitled "Surgical Instrument with Fluid Fillable Buttress," published Mar. 14, 2013, issued as U.S. Pat. No. 9,999,408 on Jun. 19, 2018, the disclosure of which is incorporated by reference herein; U.S. Patent Pub. No. 2013/0068820, entitled "Fibrin Pad Matrix with Suspended Heat Activated Beads of Adhesive," published Mar. 21, 2013, issued as U.S. Pat. No. 8,814025, on Aug. 26, 2014, the disclosure of which is incorporated by reference herein; U.S. Patent Pub. No. 2013/0082086, entitled "Attachment of Surgical Staple Buttress to Cartridge," published Apr. 4, 2013, issued as U.S. Pat. No. 8,899,464 on Dec. 2, 2014, the disclosure of which is incorporated by reference herein; U.S. Patent Pub. No. 2013/0037596, entitled "Device for Applying Adjunct in Endoscopic Procedure," published Feb. 14, 2013, issued as U.S. Pat. No. 9,492,170, on Nov. 15, 2016, the disclosure of which is incorporated by reference herein; U.S. Patent Pub. No. 2013/0062393, entitled "Resistive Heated Surgical Staple Cartridge with Phase Change Sealant," published Mar. 14, 2013, issued as U.S. Pat. No. 8,998,060 on Apr. 7, 2015, the disclosure of which is incorporated by reference herein; U.S. Patent Pub. No. 2013/0075446, entitled "Surgical Staple Assembly with Hemostatic Feature," published Mar. 28, 2013, issued as U.S. Pat. No. 9,393,018 on Jul. 19, 2016, the disclosure of which is incorporated by reference herein; U.S. Patent Pub. No. 2013/0062394, entitled "Surgical Staple Cartridge with Self-Dispensing Staple Buttress," published Mar. 14, 2013, issued as U.S. Pat. No. 9,101,359 on Aug. 11, 2015, the disclosure of which is incorporated by reference herein; U.S. Patent Pub. No. 2013/0075445, entitled "Anvil Cartridge for Surgical Fastening Device," published Mar. 28, 2013, issued as U.S. Pat. No. 9,198,644 on Dec. 1, 2015, the disclosure of which is incorporated by reference herein; U.S. Patent Pub. No. 2013/0075447, entitled "Adjunct Therapy for Applying Hemostatic Agent," published Mar. 28, 2013, now abandoned, the disclosure of which is incorporated by reference herein; U.S. Patent Pub. No. 2013/0256367, entitled "Tissue Thickness Compensator Comprising a Plurality of Medicaments," published Oct. 3, 2013, issued as U.S. Pat. No. 9,211,120 on Dec. 15, 2015, the disclosure of which is incorporated by reference herein; U.S. patent application Ser. No. 14/300,954, entitled "Adjunct Materials and Methods of Using Same in Surgical Methods for Tissue Sealing," filed Jun. 10, 2014, issued as U.S. Pat. No. 10,172,611 on Jan. 8, 2019, the disclosure of which is incorporated by reference herein; U.S. patent application Ser. No. 14/827,856, entitled "Implantable Layers for a Surgical Instrument," filed Aug. 17, 2015, issued as U.S. Pat. No. 10,835,249 on Nov. 17, 2020, the disclosure of which is incorporated by reference herein; U.S. patent application Ser. No. 14/840,613, entitled "Drug Eluting Adjuncts and Methods of Using Drug Eluting Adjuncts," filed Aug. 31, 2015, issued as U.S. Pat. No. 10,569,071, on Feb. 25, 2020, the disclosure of which is incorporated by reference herein; U.S. patent application Ser. No. 14/871,071, entitled "Compressible Adjunct with Crossing Spacer Fibers," filed Sep. 30, 2015, issued as U.S. Pat. No. 10,433,846, on Oct. 8, 2019, the disclosure of which is incorporated by reference herein; and/or U.S. patent application Ser. No. 14/871,131, entitled "Method for Applying an Implantable Layer to a Fastener Cartridge," filed Sep. 30, 2015, published as U.S. Pub. No. 2017/0086842 on Mar. 30, 2017, the disclosure of which is incorporated by reference herein.

In the present example, adhesive layer (104) is provided on buttress body (102) in order to adhere buttress body (102) to underside (65) of anvil (60). Similarly, adhesive layer (114) is provided on buttress body (112) in order to adhere buttress body (112) to deck (73) of staple cartridge (70). Adherence of the buttress body (102) to underside (65) of anvil (60) or to deck (73) of staple cartridge (70) can occur through a variety of mechanisms including but not limited to a pressure sensitive adhesive. In some versions, each adhesive layer (104, 114) comprise a pressure sensitive adhesive material. Examples of various suitable materials that may be used to form adhesive layers (104, 114) are disclosed in U.S. patent application Ser. No. 14/667,842, entitled "Method of Applying a Buttress to a Surgical Stapler," filed Mar. 25, 2015, issued as U.S. Pat. No. 10,349,939, on Jul. 16, 2019, the disclosure of which is incorporated by reference herein. Alternatively, any other suitable materials may be used. It should be understood that the term "adhesive," as used herein, may include (but is not limited to) tacky materials and also materials that are pliable or wax-like and adhere to a complex geometry via deformation and conformance. Some suitable adhesives may provide such pliability to adhere to a complex geometry via deformation and conformance without necessarily providing a high initial tack. In some instances, adhesives with lower tackiness may be removed more cleanly from surfaces. Various suitable materials that may be used to form adhesive layers (104, 114) will be apparent to those of ordinary skill in the art in view of the teachings herein.

B. Exemplary Materials and Techniques for Providing Adhesion of Buttress to Surgical Stapler As noted above, a buttress assembly (100) may include a layer (104, 114) of adhesive material (or other form of adhesive material) that adheres buttress body (102, 112) to either underside (65) of anvil (60) or deck (73) of staple cartridge (70). Such an adhesive material may provide proper positioning of buttress body (102, 112) before and during actuation of end effector (40); then allow buttress body (102, 112) to separate from end effector (40) after end effector (40) has been actuated, without causing damage to buttress body (102, 112) that is substantial enough to compromise the proper subsequent functioning of buttress body (102, 112).

Figure 5:
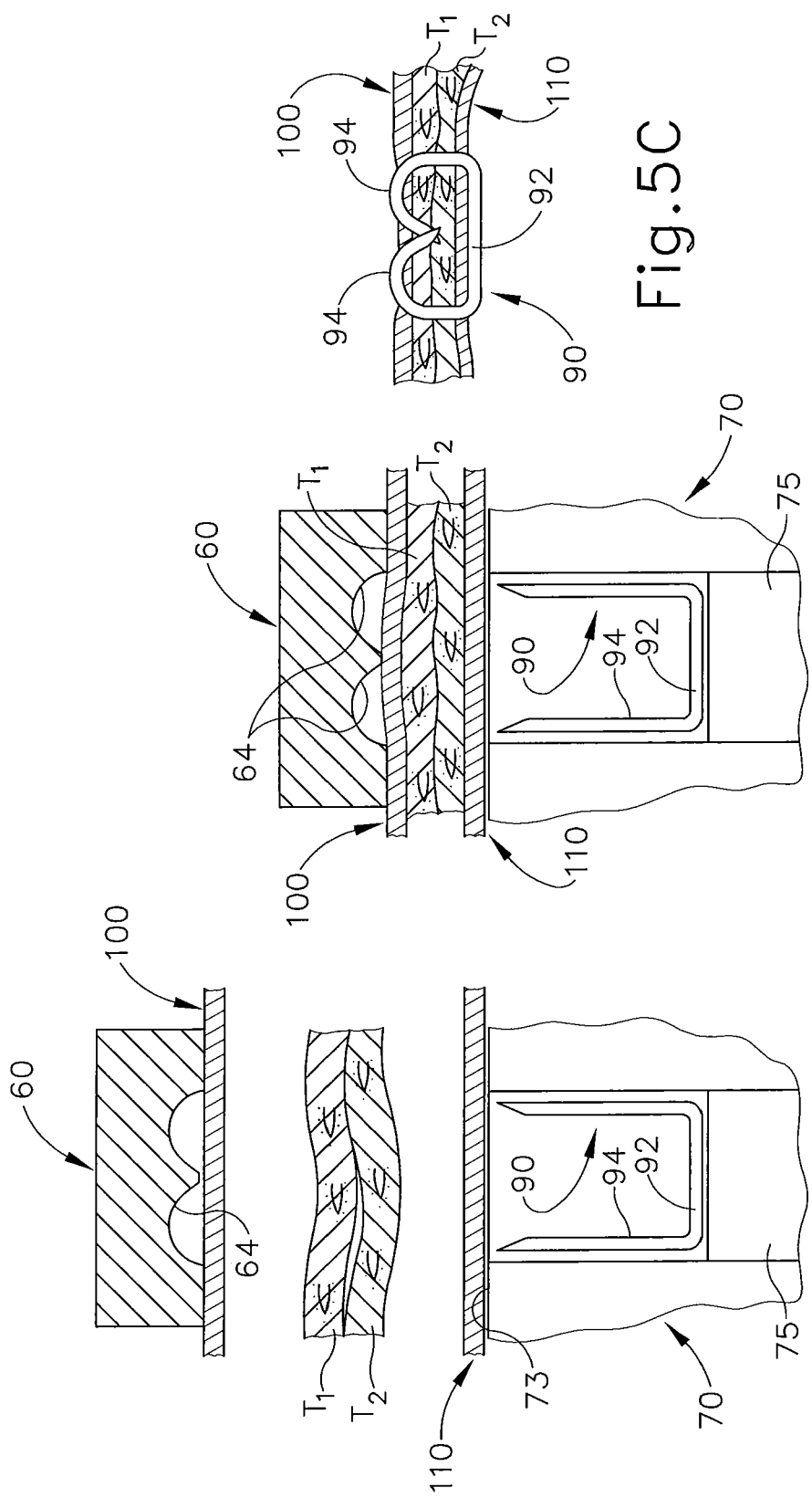
FIG. 5A depicts a cross-sectional end view of a portion of the end effector of FIG. 2 with a buttress assembly formed by the buttresses of FIG. 4 applied to the end effector, with tissue positioned between the buttresses in the end effector, and with the anvil in an open position.
FIG. 5B depicts a cross-sectional end view of the combined end effector and buttress assembly of FIG. 5A, with tissue positioned between the buttresses in the end effector, and with the anvil in a closed position.
FIG. 5C depicts a cross-sectional view of a staple and the buttress assembly of FIG. 5A having been secured to the tissue by the end effector of FIG. 2.

FIGS. 5A-5C show a sequence where an end effector (40) that has been loaded with buttress assemblies (100, 110) is actuated to drive staples (90) through two apposed layers of tissue ($T_1$, $T_2$), with buttress assemblies (100, 110) being secured to the same layers of tissue ($T_1$, $T_2$) by staples (90). In particular, FIG. 5A shows layers of tissue ($T_1$, $T_2$) positioned between anvil (60) and staple cartridge (70), with anvil (60) in the open position. Buttress assembly (100) is adhered to the underside (65) of anvil (60) via adhesive layer (104); while buttress assembly (110) is adhered to deck (73) of staple cartridge (70) via adhesive layer (114). Layers of tissue ($T_1$, $T_2$) are thus interposed between buttress assemblies (100, 110). Next, trigger (24) is pivoted toward pistol grip (22) to drive closure tube (32) and closure ring (36) distally. This drives anvil (60) to the closed position as shown in FIG. 5B. At this stage, layers of tissue ($T_1$, $T_2$) are compressed between anvil (60) and staple cartridge (70), with buttress assemblies (100, 110) engaging opposite surfaces of tissue layers ($T_1$, $T_2$). End effector (40) is then actuated as described above, driving staple (90) through buttress assemblies (100, 110) and tissue (90). As shown in FIG. 5C, crown (92) of driven staple (90) captures and retains buttress assembly (110) against layer of tissue ($T_2$). Deformed legs (94) of staple (90) capture and retain buttress assembly (100) against layer of tissue ($T_1$).

Figure 6:
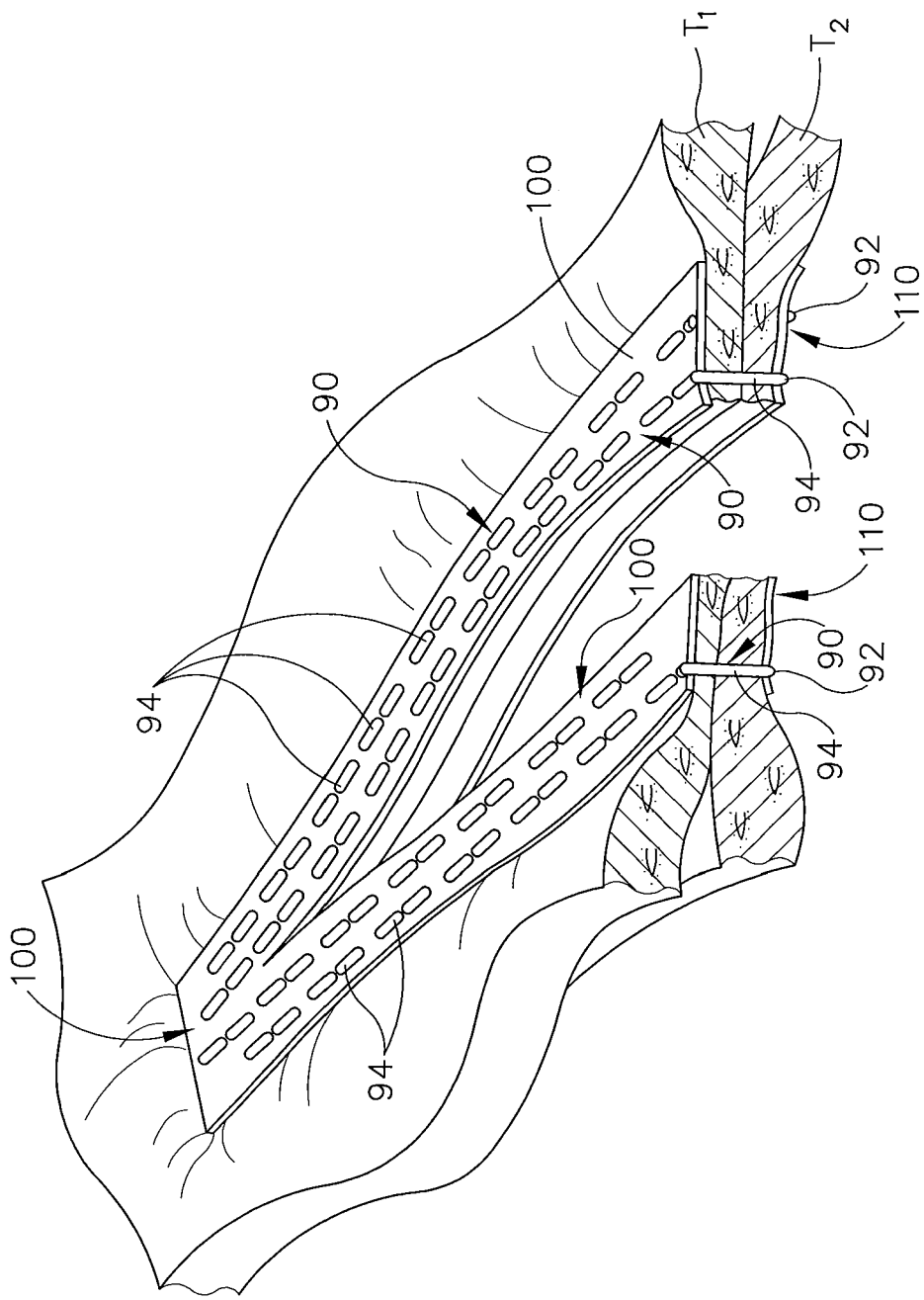
FIG. 6 depicts a perspective view of staples and the buttress assembly of FIG. 5A having been secured to the tissue by the end effector of FIG. 2.

It should be understood that a series of staples (90) will similarly capture and retain buttress assemblies (100, 110) against layers of tissue ($T_1$, $T_2$), thereby securing buttress assemblies (100, 110) to tissue ($T_1$, $T_2$) as shown in FIG. 6. As end effector (40) is pulled away from tissue (90) after deploying staples (90) and buttress assemblies (100, 110), buttress assemblies (100, 110) disengage end effector (40), such that buttress assemblies (100, 110) remain secured to tissue ($T_1$, $T_2$) with staples (90). Buttress tissue ($T_1$, $T_2$) thus provide structural reinforcement to the lines of staples (90). As can also be seen in FIG. 6, knife member (80) also cuts through a centerline of buttress tissue assemblies (100, 110), separating each buttress assemblies (100, 110) into a corresponding pair of sections, such that each section remains secured to a respective severed region of tissue ($T_1$, $T_2$).

In the foregoing example, buttress assembly (100) is sized to span across the full width of underside (65), such that buttress assembly (100) spans across channel (62). Thus, knife member (80) cuts through buttress assembly (100) during actuation of end effector (40) as described above. In some other examples, such as those described below, buttress assembly (100) is provided in two separate, laterally spaced apart portions, with one portion being disposed on underside (65) on one side of channel (62) and another portion being disposed on underside (65) on the other side of channel (62). In such versions, buttress assembly (100) does not span across channel (62), such that knife member (80) does not cut through buttress assembly (100) during actuation of end effector (40).

Likewise, buttress assembly (110) may be sized to span across the full width of deck (73), such that buttress assembly (110) spans across channel (72), and such that knife member (80) cuts through buttress assembly (110) during actuation of end effector (40) as described above. Alternatively, buttress assembly (110) may be provided in two separate, laterally spaced apart portions, with one portion being disposed on deck (73) on one side of channel (72) and another portion being disposed on deck (73) on the other side of channel (72), such that buttress assembly (110) does not span across channel (72), and such that knife member (80) does not cut through buttress assembly (110) during actuation of end effector (40).

III. TECHNIQUES FOR PROVIDING AND/OR IMPROVING ADHESION OF BUTTRESS TO WET END EFFECTOR

One of ordinary skill in the art will recognize that, during some uses of instrument (10), the operator may need to actuate end effector (40) several times within a patient. Each actuation may require the operator to remove end effector (40) from the patient, reload a new staple cartridge (70) into lower jaw (50), apply new buttress assemblies (100, 110) to anvil (60) and staple cartridge (70), and then insert the reloaded end effector (40) into the patient. Each time end effector (40) is removed from the patient, anvil (60) may be substantially wet with bodily fluids from the patient and/or other fluids in the surgical field. Even when a new cartridge (70) is installed in lower jaw (50), the new cartridge (70) may also receive fluids from other portions of end effector (40) that were already wet. The presence of fluids on underside (65) of anvil (60) and/or on deck (73) of staple cartridge (70) may make it difficult to adhere buttress assemblies (100, 110) to anvil (60) and staple cartridge (70). The following examples relate to various compositions and configurations that may be used to promote proper adhesion of buttress assemblies (100, 110) to anvil (60) and staple cartridge (70) when buttress assemblies (100, 110) to anvil (60) and staple cartridge (70) are wet with one or more fluids.

A. Adhesion of Buttress to Wet End Effector Using Humidity Tolerant Adhesive Materials In some surgical applications, it may be desirable to provide a buttress body (102, 112) with one or more humidity tolerant adhesive materials that will at least temporarily adhere to a wet end effector (40), particularly when it is being used intraoperatively. In some instances, humidity tolerant adhesive materials may provide for temporary attachment of a buttress body (102, 112) to the wet deck (73) of staple cartridge (70) or the wet underside (65) of anvil (60). A humidity tolerant adhesive material is defined herein as an adhesive material that holds a buttress body (102, 112) in place on an anvil (60) or staple cartridge (70) for at least five minutes in an environment of 100% relative humidity (e.g., in a patient's body, at a normal body temperature of approximately 37° C.), preferably after the buttress body (102, 112) has been exposed to a relative humidity of from about 20% to about 60% for up to one hour at room temperature (e.g., between approximately 20° C. and approximately 22° C.). In some instances, a humidity tolerant adhesive material may hold a buttress body (102, 112) in place on an anvil (60) or staple cartridge (70) for at least ten minutes in an environment of 100% relative humidity (e.g., in a patient's body, at a normal body temperature of approximately 37° C.), preferably after the buttress body (102, 112) has been exposed to a relative humidity of from about 20% to about 60% for up to one hour at room temperature (e.g., between approximately 20° C. and approximately 22° C.). A pressure sensitive humidity tolerant adhesive material is defined herein as a humidity tolerant adhesive material that can be transferred from a delivery device onto an anvil (60) or staple cartridge (70) by the pressure respectively exerted by the anvil (60) or staple cartridge (70).

As noted above, FIG. 4 shows buttress assemblies (100, 110) that each comprises a buttress body (102, 112) and an adhesive layer (104, 114). Adhesive layers (104, 114) respectively provide for temporary attachment of the buttress bodies (102, 112) to underside (65) of anvil (60) and deck (73) of staple cartridge (70). It should be understood that the humidity tolerant adhesive material need not necessarily constitute a separate adhesive layer (104, 114) that is discretely identifiable as being different from a layer defined by buttress body (102, 112). Examples of humidity tolerant adhesive materials that may be otherwise integrated onto or into a buttress body (102, 112) are described in further detail below.

In some instances, the humidity tolerant adhesive materials (e.g., one or more layers (104, 114)) for a buttress body (102, 112), comprise polymers that are either bioabsorbable or of a molecular weight that is sufficiently low so as to be cleared from the patient's body (e.g., less than approximately 30,000 KDa). Various physiomechanical properties of polymers may be modified in order to provide different adhesive properties. Such variable characteristics include but are not limited to the following: copolymer composition; copolymer architecture (e.g., random vs. block configurations, polymer branching, etc.); glass transition temperature (Tg); molecular weight; crystallinity; sequence distribution; copolymer chain composition; melting temperature (Tm); solubility or dissolution rate; rheological properties; surface tension; and combinations thereof. Several exemplary combinations of these variables will be provided below, though it should be understood that these examples are merely illustrative.

In addition or in the alternative to the aforementioned modifications to the physiomechanical properties of polymers, some exemplary humidity tolerant adhesive materials may comprise polymers that are combined with sorbents. Useful sorbents may be selected from the group consisting of: polysaccharides such as cellulose; cellulose derivatives, e.g., sodium carboxymethylcellulose (Na-CMC); starch; starch derivates; natural gums, e.g., agar and alginates; chitosan; pectin; gelatin; and combinations thereof. In some examples, a hydrocolloid of one or more sorbents may be mixed with the polymers. In some examples, the humidity tolerant adhesive material comprises a blend of sorbent and polymer in a ratio in a range of 70:30 sorbent to polymer, more particularly in a range of 50:50 sorbent to polymer, more preferably in a range of 10:90 sorbent to polymer. Generally it is theorized, but in no way limits the scope of this invention, that sorbents may act to absorb moisture away from the surface interface between the humidity tolerant adhesive material and the surface to which it is adhered (e.g., a wet end effector (40)), and to maintain the adherence of the buttress body (102, 112) to said surface until such time as the buttress body (102, 112) is deployed or released from end effector (40) (see, for example, FIG. 5C).

One of the aforementioned physiomechanical properties of polymers is glass transition temperature (Tg). Glass transition temperature is the temperature at which the mechanical properties of a copolymer change dramatically from a flowable adhesive to a brittle plastic. It may thus be of importance that the glass transition temperature (Tg) is sufficiently below the operating temperature of the humidity tolerant adhesive material in order to allow for sufficient polymer chain mobility. The melting temperature (Tm) of a polymer may be referred to as the "first-order transition," which is where the polymer changes state from solid to liquid. Crystalline polymers have a true melting point, which is the temperature at which the crystallites melt and the total mass of plastic becomes liquid. Amorphous polymers do not have a true melting point, but they do have a first-order transition wherein their mechanical behavior transitions from a rubbery nature to viscous rubbery flow. Suitable polymers for use in humidity tolerant adhesive materials may be semi-crystalline, i.e., they may have both amorphous and crystalline segments. Suitable polymers may have a melting point that is sufficiently above the operating temperature of the humidity tolerant adhesive material to maintain cohesive strength and to provide dimensional stability of the applied humidity tolerant adhesive material.

The molecular weight of non-bioabsorbable polymers should be high enough to provide mechanical strength to the resulting adhesive material in order to avoid cohesive failure, yet low enough that they can be cleared by the patient's body. In the case of biodegradable polymers, an upper limit on molecular weight may not be required to provide polymer breakdown products are small enough to be cleared by the patient's body.

The solubility or dissolution rate of polymers in the aqueous environments that may be encountered during surgery depend upon a number of polymer characteristics including, but not limited to: polymer composition; polymer architecture; degree of cross-linking; block length; crystallinity; molecular weight; branching; and combinations thereof. In illustrative examples described below, certain polymers and co-polymers are chosen and combined with these characteristics in mind in order to decrease the dissolution rate of the resulting humidity tolerant adhesive materials that are of use for adhering a buttress body (102, 112) to a wet end effector (40) during surgery, and maintaining the adherence of the buttress body to the wet end effector (40) until such time as the buttress body (102, 112) is deployed or released from end effector (40) (see, for example, FIG. 5C).

The surface tension and rheology of polymers present in a humidity tolerant adhesive material may also impact its adhesive properties. For example, if there is a sufficiently large mismatch between the surface tension of the polymers and the surfaces to which it will adhere, adhesion between the two may be energetically unfavorable. Similarly, the rheological properties of the polymer such as bulk modulus may be such that the humidity tolerant adhesive material can flow to conform to the surface topography of the end effector (40), while at the same time providing sufficient integrity to maintain cohesive strength and resist shearing and peeling of the buttress body (102, 112) from the end effector (40).

1. Exemplary Humidity Tolerant Adhesive Materials Comprising Poloxamer Blends

In some examples, the humidity tolerant adhesive materials (e.g., one or more of layers (104, 114)) for a buttress body (102, 112) may comprise a blend of "plastic fats", more particularly, poloxamers. In illustrative examples, the blend of poloxamers may comprise a blend of poloxamers selected from the group consisting of: poloxamer 188, for example Kolliphor® P188 from BASF (Florham Park, N.J.); Synperonic® PE/P84 from Croda Inc. (Edison, N.J.); poloxamer 124, for example Pluronic® L44 from BASF (Florham Park, N.J.); poloxamer 407, for example Pluronic® F-127 from BASF (Florham Park, N.J.); and combinations thereof. Preferably, the poloxamers are of National Formulary grade. The resulting poloxamer-based humidity tolerant adhesive materials may be putty-like materials with a relatively low crystallinity and low glass transition temperature (Tg). Generally it is theorized, but in no way limits the scope of this invention, that the presence of polypropylene oxide repeat units in the backbone of the poloxamers provides for a poloxamer blend having a slower dissolution rate, which may desirably provide for humidity tolerant adhesive materials having a greater humidity (i.e., wetness) tolerance. In turn, a buttress body (102, 112), to which poloxamer-based adhesive materials have been applied, may desirably remain adhered to a wet end effector (40) of a surgical stapling instrument (10) during a surgical procedure until such time as buttress body (102, 112) is deployed (see, for example, FIG. 5C).

In some examples, the humidity tolerant adhesive materials comprise a poloxamer blend of poloxamer 188 and Synperonic® PE/P84 in a molar ratio in the range of from 1:3 to 1:4 of poloxamer 188 to Synperonic® PE/P84. In some other examples, humidity tolerant adhesive materials comprise a poloxamer blend of poloxamer 188 and poloxamer 124 in a molar ratio in the range of from about 1:1 to about 1:4, more particularly from about 1:1.5 to about 1:3, of poloxamer 188 to poloxamer 124. In yet some other examples, the poloxamer blend may comprise a blend of poloxamer 407 and poloxamer 124 in a molar ratio in the range of from about 1:1, to about 1:5, more particularly from about 1:1.5 to about 1:3 of poloxamer 407 to poloxamer 124.

In yet some other examples, the poloxamers may be combined with non-ionic surfactants to modify the hydrophobicity of the resulting humidity tolerant adhesive material. In some such examples, the poloxamers may be combined with non-ionic surfactants selected from the group consisting of: polysorbates; polyethylene glycol hexadecyl ether, for example Brij 52 from Croda Inc. (Edison, N.J.); sorbitane monooleate, for example, Span® 80 from Sigma Aldrich (Saint Louis, Mo.); and combinations thereof.

In each of the foregoing exemplary poloxamer blends, it may be important to control the crystallite size of the poloxamers in order to achieve the desirable adhesive characteristics in the resulting humidity tolerant adhesive material.

2. Exemplary Humidity Tolerant Adhesive Materials Comprising Polyethylene Glycol or Polyethylene-Polyethylene Glycol Co-polymer In some examples, the humidity tolerant adhesive materials (e.g., one or more of layers (104, 114)) for a buttress body (102, 112) comprise polyethylene glycol (PEG) or polyethylene-polyethylene glycol co-polymers (PE-co-PEG). The resulting humidity tolerant adhesive materials may be putty-like, malleable and extrudable.

In yet further examples, the pressure sensitive humidity tolerant adhesive materials comprise, or consist essentially of, polyethylene-polyethylene glycol co-polymers (PE-co-PEG) with a molecular weight that is sufficiently low so as to be cleared from the patient's body (e.g., less than approximately 30,000 KDa).

In yet further examples, the humidity tolerant adhesive materials comprise a blend of polyethylene-polyethylene glycol copolymers (PE-co-PEG) and poly(caprolactone)-glycolide copolymers (PCL/PGA) in the ratio of about 40:60

PCL:PGA, preferably in a ratio of about 50:50 PCL:PGA, more preferably in a ratio of about 60:40 PCL:PGA. Such a blend may have low crystallinity and may even be near amorphous.

In yet further examples, the humidity tolerant adhesive materials comprise a blend of polyethylene glycol having different molecular weights that is in turn blended with a polymer or co-polymer selected from the group consisting of: poloxamers; poly(caprolactone)-glycolide copolymers (PCL/PGA); lactide (PLA); and combinations thereof. By way of example only, the blend may include polyethylene glycol 3350 (PEG 3350), polyethylene glycol 400 (PEG 400), and/or other polyethylene glycols.

In yet further examples, the humidity tolerant adhesive materials comprise a block copolymer of polyethylene glycol 20,000 (PEG 20,000) and poly(caprolactone)-glycolide copolymers (PCL/PGA) that are characterized by a molar ratio of 65:35 poly(caprolactone) (PCL) to glycolide (PGA). The resulting blends may have a relatively high molecular weight and lower solubility.

As yet another merely illustrative example, the humidity tolerant adhesive materials comprise a blend of other water soluble copolymers with poloxamers or PEG, with a molecular weight low enough to be cleared from the patient's body. Such a blend may be substituted for a component of any of the blends described above; or for the entirety of any of the blends described above. By way of further example only, the polymer(s) in such a blend may be biodegradable such as PCL/PGA, etc.

3. Exemplary Humidity Tolerant Adhesive Materials Comprising Solid Triglycerides in Oil In some examples, the humidity tolerant adhesive materials (e.g., one or more of layers (104, 114)) for a buttress body (102, 112) comprise "plastic fats" comprising solid triglycerides in oil. In some illustrative examples, such humidity tolerant adhesive materials further comprise sorbents. Useful sorbents may be selected from the group consisting of: polysaccharides such as cellulose; cellulose derivatives, e.g., sodium carboxymethylcellulose (Na-CMC); starch; starch derivates; natural gums, e.g., agar and alginates; chitosan; pectin; gelatin; and combinations thereof. Useful triglycerides may be selected from the group consisting of: decanoyl glycerides; octanoyl glycerides; and combinations thereof—for example, Miglyol® 810, 812, 818 and 829 from Caesar & Loretz GMBH (Hilden, Del.). Useful oils may be selected from the group consisting of: bis-diglyceryl polyacyladipate-1; glycerol trioheptanoate; and combinations thereof—for example, Softisan® 645 and Spezialöl 107 from Cremer Care (Hamburg, GE). The resulting humidity tolerant adhesive materials may desirably provide for good adhesion to end effector (40) and good spreading properties.

4. Exemplary humidity Tolerant Adhesive Materials Comprising Hydrocolloid Gels In some examples, the humidity tolerant adhesive materials (e.g., one or more of layers (104, 114)) for a buttress body (102, 112) comprise hydrocolloid gels. In some illustrative examples, useful hydrocolloid gels may be selected from the group consisting of gels comprising: chitosan; carboxymethyl cellulose (CMC); ethyl cellulose; hydroxypropylmethyl cellulose; gelatin; and combinations thereof. The resulting humidity tolerant adhesive materials may have a relatively high water binding capacity.

B. Exemplary Patterning of Humidity Tolerant Adhesive Materials on Buttress Body Patterning of humidity tolerant adhesive material on a buttress body (102, 112) may be utilized to impact the strength of the adhesive bond of the buttress body (102, 112) to an end effector (40), particularly a wet end effector (40). In exemplary embodiments in which it is desired to reduce the overall adhesion of a buttress body (102, 112) to an end effector (40) so that it may be more easily deployed or released from end effector (40) (as in FIG. 5C for example), the humidity tolerant adhesive material may be applied to a buttress body (102, 112) in a pattern selected from the group consisting of: stripes; discrete dots; lattices; and combinations thereof. Conversely, in exemplary embodiments in which it is desired to increase the overall adhesion of a buttress body (102, 112) to an end effector (40) so that it less readily deployed or released from end effector (40) (as in FIG. 5C for example), the humidity tolerant adhesive materials may be applied in an adhesive layer (104, 114), that extends continuously along the entire surface of buttress body (102, 112).

Figure 7:
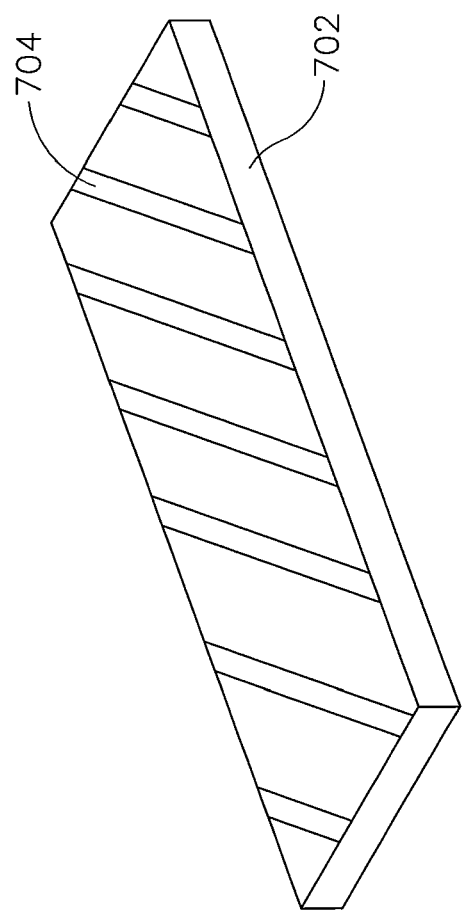
FIG. 7 depicts a perspective view of an exemplary alternative buttress assembly.

FIG. 7 shows an exemplary buttress body (702) in which humidity tolerant adhesive material is applied to the buttress body (702) in a pattern of obliquely oriented stripes (704). Generally it is theorized, but in no way limits the scope of this invention, that oblique stripes (704) present a continuous line to resist side loads that may be encountered during surgery by a buttress body (704) that has been adhered to an end effector (40). In addition, it is believed that oblique stripes (704) minimize the percentage of area that is coated by the adhesive material along the axis of the buttress body (702) in the direction of the forces that will release the buttress body (702), so as allow the buttress body (702) to be readily deployed from the end effector (40) during a surgical procedure (as in FIG. 5C for example). In the present example, oblique stripes (704) are oblique in the sense that stripes (704) extend along paths that are obliquely oriented relative to axes that are parallel to the longitudinal axis of buttress body (702). In some exemplary variations, stripes (704) extend along axial paths that are parallel to the longitudinal axis of buttress body (702).

Figure 8:
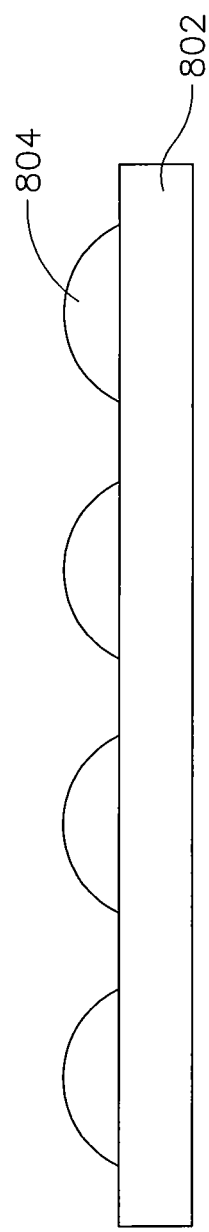
FIG. 8 depicts a cross-sectional side view of another exemplary alternative buttress assembly.

FIG. 8 depicts a perspective view of an exemplary buttress body (802) in which humidity tolerant adhesive material has been applied in a pattern of discrete, semi-rigid dots (804). The discrete, rigid semi-dots (804) may be sized and positioned to correspond with the positioning of staple forming pockets (64) of anvil (60). Thus, the discrete, semi-rigid dots of adhesive material (804) are may be arranged in four longitudinally extending linear arrays, with each longitudinally extending linear array corresponding the longitudinally arrayed arrangement of staple forming pockets (64) of anvil (60). Alternatively, any other suitable arrangement may be used. Generally it is theorized, but in no way limits the scope of this invention, that adding the rigid dots (804) boosts the modulus of the humidity tolerant adhesive material, while having little impact on its cohesive strength.

Figure 9:
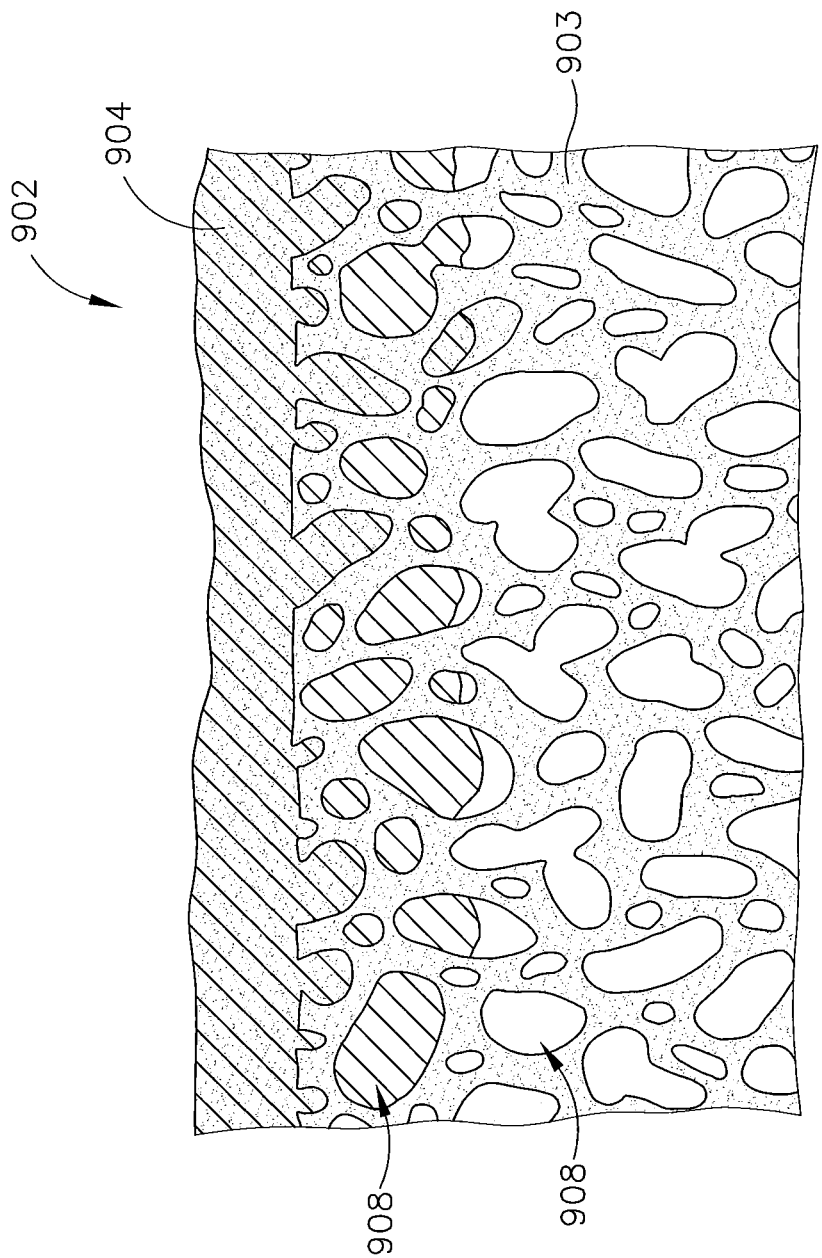
FIG. 9 depicts a cross-sectional side view of another exemplary alternative buttress assembly.

FIG. 9 shows how buttress body (902) provides a lattice defining a plurality of cells (908). Due to the presence of cells (908) and the porous nature of buttress body (902), when the humidity tolerant adhesive material (904) is applied to the buttress body (902), it forms a lattice pattern by entering into some of those cells (908), thereby partially infusing buttress body (902) with the adhesive material. In other words, buttress body (902) acts like a sponge absorbing the adhesive material, allowing the adhesive material to deform, surround, and essentially grab hold of the lattice connections within buttress body (902).

In some instances, the humidity tolerant adhesive material is initially applied to buttress body (902) when the adhesive material is in a relatively highly viscous form. Buttress body (902) is then heated to decrease the viscosity of the adhesive material, causing the adhesive material to enter some of the cells (908) of buttress body (902). Buttress body (902) is then cooled or allowed to cool, causing the viscosity of the adhesive material to increase back to its previous state. Buttress body (902) may then be heated again as buttress body (902) is being applied to end effector (40) as described above. In some other versions, the adhesive material already has a low enough viscosity to enter cells (908) when the adhesive material is applied, without requiring the adhesive material to be heated. In other words, the adhesive material may wick into cells (908) of buttress body (902). In some such versions, a protective film (e.g., polytetrafluoroethylene (PTFE)) may be applied over the adhesive material to protect and/or contain the adhesive material before buttress body (902) is applied to end effector (40). Other suitable ways in which buttress assembly (902) may be formed and provided are disclosed in U.S. patent application Ser. No. 14/667,842, entitled "Method of Applying a Buttress to a Surgical Stapler," filed Mar. 25, 2015, issued as U.S. Pat. No. 10,349,939, on Jul. 16, 2019, the disclosure of which is incorporated by reference herein.

C. Reduction of Spontaneous Separation of Buttress from Humidity Tolerant Adhesive Material In some surgical applications, it may be desirable to reduce the spontaneous separation of a buttress body (102, 112) from the humidity tolerant adhesive material that has been applied thereto. Such spontaneous separation or "dewetting" may occur as a result of moisture being present on the end effector (40) to which the buttress body (102, 112) has been adhered. In some instances, de-wetting may be minimized by one or more steps selected from the group consisting of: drying; priming; absorbing water; and combinations thereof. Each of these steps is explained in further detail below.

In some instances, de-wetting may be minimized by drying the end effector (40) prior to adhering a buttress body (102, 112) thereto. In exemplary embodiments, drying the end effector (40) may be accomplished by applying an absorbent to the end effector (40). For instance, end effector (40) may be temporary clamped onto an absorbent platform (e.g., comprising a polyacrylate pad) in order to substantially dry underside (65) of anvil (60) and deck (73) of staple cartridge (70) as described in U.S. Patent App. No. 62/209,041, entitled "Method and Apparatus for Applying a Buttress to an End Effector of a Surgical Stapler," filed Aug. 24, 2015, the disclosure of which is incorporated by reference herein. Other suitable ways in which end effector (40) may be dried prior to adhering a buttress body (102, 112) thereto will be apparent to those of ordinary skill in the art in view of the teachings herein.

In some instances, de-wetting may be additionally or alternatively minimized by priming the end effector (40) with a hydrophobic layer prior to adhering a buttress body (102, 112) thereto. In exemplary embodiments, a sponge with an adhesive-miscible hydrophobe may be clamped onto the end effector (40) to make it temporarily hydrophobic prior to adhering a buttress body (102, 112) thereto. In exemplary embodiments, adhesive-miscible hydrophobes may be selected from the group consisting of: ethyl citrate; triacetin; triolein; and combinations thereof.

In some versions, the adhesive-miscible hydrophobes may be applied as follows.

One or more adhesive-miscible hydrophobes may be pre-loaded into an open cell foam layer. The open cell foam layer may be loaded and squeezed between the buttress bodies (102, 112) after the buttress bodies (102, 112) have been adhered onto the anvil (60) and lower jaw (50) of the end effector (40). During squeezing of the open cell foam layer, at least a portion of the adhesive-miscible hydrophobe(s) may migrate from the open cell foam layer, through the buttress bodies (102, 112) to the interface between the humidity tolerant adhesive material and the anvil (60) or staple cartridge (70) of the end effector (40), creating a temporarily hydrophobic environment that may be favorable to maintaining good adhesive properties.

In some instances, de-wetting may be additionally or alternatively minimized by coating all or a portion of the end effector (40), e.g. the anvil (60) and/or staple cartridge (70), with a hydrophobic lubricious coating comprising calcium stearate or magnesium stearate.

In some instances, de-wetting may be additionally or alternatively minimized by absorbing moisture away from the surface of the end effector (40). In some such versions, this may be accomplished by mixing a hydrocolloid into the humidity tolerant adhesive material at the time that the adhesive is made. Generally it is theorized, but in no way limits the scope of this invention, that hydrocolloids provide the resulting humidity tolerant adhesive material with wet tack characteristics that enable the adhesive material to stick to both wet and dry surfaces. Suitable compositions that may form the hydrocolloid may be selected from the group consisting of: carboxy methylcellulose (CMC); gelatin; hyaluronate; and combinations thereof.

In some instances, moisture may additionally or alternatively be absorbed away from the surface of the end effector (40) by adding a hydrophilic block to one of the polymers or co-polymers that form the humidity tolerant adhesive material. Suitable hydrophilic blocks may be selected from the group consisting of: polyethylene glycol (PEG); polyvinyl pyrrolidine (PVP); and combinations thereof.

D. Reduction of Forces on Buttress Bodies Against Tissue

As noted above in reference to FIG. 6, a series of staples (90) may capture and retain buttress assemblies (100, 110) against layers of tissue ($T_1$, $T_2$), thereby securing buttress assemblies (100, 110) to tissue ($T_1$, $T_2$). In some surgical procedures, it may be desirable to reduce forces that are exerted against the buttress assemblies (100, 110) when they are being placed, or are in place, against the layers of tissue ($T_1$, $T_2$). Such a reduction in force may allow for better adhesion of the buttress bodies (102, 112) to the end effector (40). In addition, or in the alternative, it may be desirable to reduce forces that may damage the layers of tissue ($T_1$, $T_2$) that are to be, or have been, secured. In illustrative examples, this may be accomplished by treating the tissue-contacting surfaces of one or more buttress assemblies (100, 110) so that they become lubricious. Generally it is theorized, but in no way limits the scope of this invention, that a lubricious buttress body (102, 112) surface may reduce the shear force, i.e., drag force, that is applied between the layers of tissue ($T_1$, $T_2$) and buttress assemblies (100, 110). Exemplary substances that may be applied to the tissue-contacting surfaces of one or more buttress assemblies (100, 110) to make them lubricious may be selected from the group consisting of: polyethylene glycol 200 (PEG 200); silicone; oil; and combinations thereof.

In further illustrative examples, forces may additionally or alternatively be reduced by modifying the edges of the buttress body assembly (100, 110). Generally it is theorized, but in no way limits the scope of this invention, that such modifications of the edges of the buttress body assembly (100, 110) may minimize snagging and/or gripping on the layers of tissue ($T_1$, $T_2$) by the buttress assemblies (100, 110) when they are being placed, or are in place, against the layers of tissue ($T_1$, $T_2$), and vice versa. Useful means of modifying the edges of the buttress body assembly (100, 110) may be selected from the group consisting of: radiusing; chamfering; and combinations thereof.

In addition to the foregoing, it should also be understood that any of the various buttress assemblies described herein may be further constructed and operable in accordance with at least some of the teachings of U.S. patent application Ser. No. 14/667,842, entitled "Method of Applying a Buttress to a Surgical Stapler," filed Mar. 25, 2015, issued as U.S. Pat. No. 10,349,939 on Jul. 16, 2019, the disclosure of which is incorporated by reference herein.

IV. EXEMPLARY COMBINATIONS

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A method of applying a buttress to a wet surgical stapler end effector with a humidity tolerant adhesive, the method comprising the steps of: (a) positioning a buttress assembly between an anvil and a staple cartridge of the end effector, wherein the buttress assembly comprises: (i) a buttress body, and (ii) a humidity tolerant adhesive material, wherein the humidity tolerant adhesive material faces either an underside of the anvil or a deck of the staple cartridge, wherein the anvil is in an open position relative to the staple cartridge during the act of positioning the buttress assembly between the anvil and the staple cartridge; (b) moving the anvil toward the staple cartridge; and (c) moving the anvil back to the open position, wherein the buttress assembly is adhered to the underside of the anvil or the deck of the staple cartridge via the humidity tolerant adhesive material with the anvil moved back to the open position, wherein the humidity tolerant adhesive material holds the buttress body to the underside of the anvil or the deck of the staple cartridge for at least five minutes in an environment of 100% relative humidity.

Example 2

The method of Example 1, wherein the humidity tolerant adhesive material holds the buttress body to the underside of the anvil or the deck of the staple cartridge for at least ten minutes in an environment of 100% relative humidity at body temperature after the humidity tolerant adhesive material has been exposed to a relative humidity of from about 20% to about 40% for up to one hour at room temperature.

Example 3

The method of any one or more of Examples 1 through 2, wherein the humidity tolerant adhesive material comprises a blend of poloxamers.

Example 4

The method of Example 3, wherein the poloxamers are selected from the group consisting of: poloxamer 188; Synperonic® PE/P84; poloxamer 124; poloxamer 407; and combinations thereof.

Example 5

The method of any one or more of Examples 1 through 4, wherein the humidity tolerant adhesive material comprises a mixture of polyethylene glycol having a molecular weights of from about 200 to about 20,000.

Example 6

The method of any one or more of Examples 1 through 5, wherein the humidity tolerant adhesive material comprises copolymers selected from the group consisting of: polyethylene-polyethylene glycol copolymers; poly(caprolactone)-glycolide copolymers; and combinations thereof.

Example 7

The method of Example 6, wherein the humidity tolerant adhesive material comprises a blend of polyethylene-polyethylene glycol copolymers and poly(caprolactone)-glycolide copolymers in the ratio of from about 40:60 to about 60:40 of polyethylene-polyethylene glycol copolymers to poly(caprolactone)-glycolide copolymers.

Example 8

The method of any one or more of Examples 1 through 7, wherein the humidity tolerant adhesive material comprises a block copolymer of polyethylene glycol and poly(caprolactone)-glycolide copolymer.

Example 9

The method of any one or more of Examples 1 through 8, wherein the humidity tolerant adhesive material comprises triglycerides.

Example 10

The method of any one or more of Examples 1 through 9, wherein the humidity tolerant adhesive material comprises a hydrocolloid gel.

Example 11

A buttress assembly that is configured to temporarily adhere to a wet surgical stapler end effector, the buttress assembly comprising: (a) a buttress body; and (b) humidity tolerant adhesive material, wherein the humidity tolerant adhesive material is applied to at least one side of the buttress body, wherein the humidity tolerant adhesive material is configured to hold the buttress body to an underside of an anvil or a deck of a staple cartridge for at least five minutes in an environment of 100% relative humidity at approximately 37° C.

Example 12

The buttress assembly of Example 11, wherein the humidity tolerant adhesive material is configured to hold the buttress body to the underside of the anvil or the deck of the staple cartridge for at least five minutes in an environment of 100% relative humidity at approximately 37° C. after the humidity tolerant adhesive material has been exposed to a relative humidity of from about 20% to about 60% for up to one hour at a temperature between approximately 20° C. and approximately 22° C.

Example 13

The buttress assembly of any one or more of Examples 11 through 12, wherein the humidity tolerant adhesive material comprises a blend of poloxamers.

Example 14

The buttress assembly of any one or more of Examples 11 through 13, wherein the humidity tolerant adhesive material comprises a mixture of polyethylene glycol having a molecular weights of from about 200 to about 20,000.

Example 15

The buttress assembly of any one or more of Examples 11 through 14, wherein the humidity tolerant adhesive material comprises copolymers selected from the group consisting of: polyethylene-polyethylene glycol copolymers; poly(caprolactone)-glycolide copolymers; and combinations thereof.

Example 16

The method of any one or more of Examples 11 through 15, wherein the humidity tolerant adhesive material comprises a blend of polyethylene-polyethylene glycol copolymers and poly(caprolactone)-glycolide copolymers in the ratio of from about 40:60 to about 60:40 of polyethylene-polyethylene glycol copolymers to poly(caprolactone)-glycolide copolymers.

Example 17

The buttress assembly of any one or more of Examples 11 through 16, the humidity tolerant adhesive material comprises a block copolymer of polyethylene glycol and poly(caprolactone)-glycolide copolymer.

Example 18

The buttress assembly of any one or more of Examples 11 through 17, wherein the humidity tolerant adhesive material comprises triglycerides.

Example 19

The buttress assembly of any one or more of Examples 11 through 18, wherein the wherein the humidity tolerant adhesive material comprises a hydrocolloid gel.

Example 20

A buttress assembly that is configured to temporarily adhere to a wet surgical stapler end effector, the buttress assembly comprising: (a) a buttress body; and (b) humidity tolerant adhesive material, wherein the humidity tolerant adhesive material is applied to at least one side of the buttress body, wherein the humidity tolerant adhesive material is configured to hold the buttress body to an underside of an anvil or a deck of a staple cartridge for at least five minutes in an environment of 100% relative humidity at approximately 37° C., wherein the humidity tolerant adhesive material comprises a combination of solid triglycerides in oil and one or more sorbents.

V. MISCELLANEOUS

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

In addition to the foregoing, it should also be understood that any of the various buttress assemblies described herein may be further constructed and operable in accordance with at least some of the teachings of U.S. patent application Ser. No. 14/667,842, entitled "Method of Applying a Buttress to a Surgical Stapler," filed Mar. 25, 2015, issued as U.S. Pat. No. 10,349,939 on Jul. 16, 2019, the disclosure of which is incorporated by reference herein; U.S. patent application Ser. No. 14/827,856, entitled "Implantable Layers for a Surgical Instrument," filed Aug. 17, 2015, issued as U.S. Pat. No. 10,835,249 on Nov. 17, 2020, the disclosure of which is incorporated by reference herein; U.S. patent application Ser. No. 14/871,071, entitled "Compressible Adjunct with Crossing Spacer Fibers," filed Sep. 30, 2015, issued as U.S. Pat. No. 10,433,846 on Oct. 8, 2019, the disclosure of which is incorporated by reference herein; and U.S. patent application Ser. No. 14/871,131, entitled "Method for Applying an Implantable Layer to a Fastener Cartridge," filed Sep. 30, 2015, published on U.S. Pub. No. 2017/0086842, on Mar. 30, 2017, the disclosure of which is incorporated by reference herein. Furthermore, in addition to the methods described herein, any of the various buttress assemblies described herein may be applied to end effector (40) in accordance with at least some of the teachings of U.S. Provisional Patent App. No. 62/209,041, entitled "Method and Apparatus for Applying a Buttress to End Effector of a Surgical Stapler," filed Aug. 24, 2015, the disclosure of which is incorporated by reference herein; and/or U.S. patent application Ser. No. 14/871,131, entitled "Method for Applying an Implantable Layer to a Fastener Cartridge," filed Sep. 30, 2015, published as U.S. Pub. No. 2017/0086842 on Mar. 30, 2017, the disclosure of which is incorporated by reference herein. Various suitable ways in which the teachings herein may be combined with various teachings of the above-cited references will be apparent to those of ordinary skill in the art.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of any of the following: U.S. Pat. No. 5,792,135, entitled "Articulated Surgical Instrument For Performing Minimally Invasive Surgery With Enhanced Dexterity and Sensitivity," issued Aug. 11, 1998, the disclosure of which is incorporated by reference herein; U.S. Pat. No. 5,817,084, entitled "Remote Center Positioning Device with Flexible Drive," issued Oct. 6, 1998, the disclosure of which is incorporated by reference herein; U.S. Pat. No. 5,878,193, entitled "Automated Endoscope System for Optimal Positioning," issued Mar. 2, 1999, the disclosure of which is incorporated by reference herein; U.S. Pat. No. 6,231,565, entitled "Robotic Arm DLUS for Performing Surgical Tasks," issued May 15, 2001, the disclosure of which is incorporated by reference herein; U.S. Pat. No. 6,783,524, entitled "Robotic Surgical Tool with Ultrasound Cauterizing and Cutting Instrument," issued Aug. 31, 2004, the disclosure of which is incorporated by reference herein; U.S. Pat. No. 6,364,888, entitled "Alignment of Master and Slave in a Minimally Invasive Surgical Apparatus," issued Apr. 2, 2002, the disclosure of which is incorporated by reference herein; U.S. Pat. No. 7,524,320, entitled "Mechanical Actuator Interface System for Robotic Surgical Tools," issued Apr. 28, 2009, the disclosure of which is incorporated by reference herein; U.S. Pat. No. 7,691,098, entitled "Platform Link Wrist Mechanism," issued Apr. 6, 2010, the disclosure of which is incorporated by reference herein; U.S. Pat. No. 7,806,891, entitled "Repositioning and Reorientation of Master/Slave Relationship in Minimally Invasive Telesurgery," issued Oct. 5, 2010, the disclosure of which is incorporated by reference herein; U.S. Pub. No. 2013/0012957, entitled "Automated End Effector Component Reloading System for Use with a Robotic System, published Jan. 10, 2013, issued as U.S. Pat. No. 8,844,789, on Sep. 2, 2014, the disclosure of which is incorporated by reference herein; U.S. Pub. No. 2012/0199630, entitled "Robotically-Controlled Surgical Instrument with Force-Feedback Capabilities," published Aug. 9, 2012, issued as U.S. Pat. No. 8,820,605, on Sep. 2, 2014, the disclosure of which is incorporated by reference herein; U.S. Pub. No. 2012/0132450, entitled "Shiftable Drive Interface for Robotically-Controlled Surgical Tool," published May 31, 2012, issued as U.S. Pat. No. 8,616,431, on Dec. 31, 2013, the disclosure of which is incorporated by reference herein; U.S. Pub. No. 2012/0199633, entitled "Surgical Stapling Instruments with Cam-Driven Staple Deployment Arrangements," published Aug. 9, 2012, issued as U.S. Pat. No. 8,573,461 on Nov. 5, 2013, the disclosure of which is incorporated by reference herein; U.S. Pub. No. 2012/0199631, entitled "Robotically-Controlled Motorized Surgical End Effector System with Rotary Actuated Closure Systems Having Variable Actuation Speeds," published Aug. 9, 2012, issued as U.S. Pat. No. 8,602,288 on Dec. 10, 2013, the disclosure of which is incorporated by reference herein; U.S. Pub. No. 2012/0199632, entitled "Robotically-Controlled Surgical Instrument with Selectively Articulatable End Effector," published Aug. 9, 2012, issued as U.S. Pat. No. 9,301,759 on Apr. 5, 2016,the disclosure of which is incorporated by reference herein; U.S. Pub. No. 2012/0203247, entitled "Robotically-Controlled Surgical End Effector System," published Aug. 9, 2012, issued as U.S. Pat. No. 8,783,541 Jul. 22, 2014, the disclosure of which is incorporated by reference herein; U.S. Pub. No. 2012/0211546, entitled "Drive Interface for Operably Coupling a Manipulatable Surgical Tool to a Robot," published Aug. 23, 2012, issued as U.S. Pat. No. 8,479,969 on Jul. 9, 2013; U.S. Pub. No. 2012/0138660, entitled "Robotically-Controlled Cable-Based Surgical End Effectors," published Jun. 7, 2012, issued as U.S. Pat. No. 8,800,838 Aug. 12, 2014, the disclosure of which is incorporated by reference herein; and/or U.S. Pub. No. 2012/0205421, entitled "Robotically-Controlled Surgical End Effector System with Rotary Actuated Closure Systems," published Aug. 16, 2012, issued as U.S. Pat. No. 8,573,465 on Nov. 5 2013, the disclosure of which is incorporated by reference herein.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a suitable closed and sealed container. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A buttress assembly that is configured to temporarily adhere to a wet surgical stapler end effector, the buttress assembly comprising:
   (a) a buttress body comprising a collagen matrix; and
   (b) a humidity tolerant adhesive material that comprises a de-wetting agent configured to absorb moisture, wherein the humidity tolerant adhesive material is disposed on at least one side of the buttress body.

2. The buttress assembly of claim 1, wherein the humidity tolerant adhesive material comprises polymers that are:
   (a) bioabsorbable polymers, and/or
   (b) polymers having a molecular weight of less than about 30,000 kDa.

3. The buttress assembly of claim 1, wherein the humidity tolerant adhesive material comprises sorbents selected from the group of: cellulose, cellulose derivatives, starch, starch derivates, natural gums, chitosan, pectin, gelatin and combinations thereof.

4. The buttress assembly of claim 3, wherein the sorbents comprise cellulose derivatives, and wherein the cellulose derivatives comprise carboxymethyl cellulose.

5. The buttress assembly of claim 3, further comprising a hydrophobic layer disposed between the buttress body and the humidity tolerant adhesive material, wherein the hydrophobic layer comprises adhesive-miscible hydrophobes selected from the group of: ethyl citrate, triacetin, triolein and combinations thereof.

6. The buttress assembly of claim 1, wherein the de-wetting agent comprises a hydrocolloid gel, the hydrocolloid gel in turn comprising a blend of:
   (a) one or more polymers, and
   (b) one or more sorbents;
wherein the one or more polymers and one or more sorbents are present in the humidity tolerant adhesive material at a ratio of 20:30 of sorbent to polymer.

7. The buttress assembly of claim 1, wherein the humidity tolerant adhesive material comprises a blend of polyethylene-polyethylene glycol copolymers and poly(caprolactone)-glycolide copolymers.

8. The buttress assembly of claim 1, wherein the humidity tolerant adhesive material comprises a block copolymer of polyethylene glycol and poly(caprolactone)-glycolide copolymer.

9. The buttress assembly of claim 1, wherein the humidity tolerant adhesive material is configured to hold the buttress body to an underside of an anvil or a deck of a staple cartridge for at least five minutes in an environment of 100% relative humidity at about 37° C. after the humidity tolerant adhesive material has been exposed to a relative humidity of from about 20% to about 60% for up to one hour at between about 20° C. and about 22° C.

10. A buttress assembly that is configured to temporarily adhere to a wet surgical stapler end effector, the buttress assembly comprising:
   (a) a buttress body comprising a collagen matrix; and
   (b) a humidity tolerant adhesive material disposed on at least one side of the buttress body, wherein the humidity tolerant adhesive material comprises a de-wetting agent configured to absorb moisture,
   wherein the humidity tolerant adhesive material is configured to secure the buttress body to a stapling surface of the wet surgical stapler end effector for at least five minutes in an environment of 100% relative humidity at about 37° C. after the humidity tolerant adhesive material has been exposed to a relative humidity of from about 20% to about 60% for up to one hour at between about 20° C. and about 22° C.

11. The buttress assembly of claim 10, wherein the humidity tolerant adhesive material comprises:
   (a) bioab sorb able polymers, and/or
   (b) polymers having a molecular weight of less than about 30,000 kDa.

12. The buttress assembly of claim 10, wherein the humidity tolerant adhesive material comprises sorbents selected from the group of: cellulose, cellulose derivatives, starch, starch derivates, natural gums, chitosan, pectin, gelatin and combinations thereof.

13. The buttress assembly of claim 12, wherein the sorbents comprise cellulose derivatives, wherein the cellulose derivatives comprise carboxymethyl cellulose.

14. The buttress assembly of claim 10, wherein the de-wetting agent comprises a hydrocolloid gel, the hydrocolloid gel in turn comprising a blend of:
   (a) one or more polymers, and
   (b) one or more sorbents;
wherein the one or more polymers and the one or more sorbents are present in the humidity tolerant adhesive material at a ratio of 20:30 of sorbent to polymer.

15. The buttress assembly of claim 10, wherein the humidity tolerant adhesive material comprises a blend of polyethylene-polyethylene glycol copolymers and poly(caprolactone)-glycolide copolymers.

16. The buttress assembly of claim 10, wherein the humidity tolerant adhesive material comprises a block copolymer of polyethylene glycol and poly(caprolactone)-glycolide copolymer.

17. The buttress assembly of claim 10, further comprising a hydrophobic layer disposed between the buttress body and the humidity tolerant adhesive material.

18. The buttress assembly of claim 17, wherein the hydrophobic layer comprises adhesive-miscible hydrophobes selected from the group of: ethyl citrate, triacetin, triolein and combinations thereof.

19. A buttress assembly that is configured to temporarily adhere to a wet surgical stapler end effector, the buttress assembly comprising:
   (a) a buttress body comprising a collagen matrix;
   (b) a humidity tolerant adhesive material; and
   (c) a hydrophobic layer disposed between the buttress body and the humidity tolerant adhesive material, wherein the humidity tolerant adhesive material comprises:
polymers selected from the group of:
(A) bioabsorbable polymers, or
(B) polymers having a molecular weight of less than about 30,000 kDa; and
(ii) sorbents selected from the group of: cellulose, cellulose derivatives, starch, starch derivates, natural gums, chitosan, pectin, gelatin and combinations thereof.

20. The buttress assembly of claim 19, wherein the humidity tolerant adhesive material comprises a de-wetting agent configured to absorb moisture.

\* \* \* \* \*